(12) United States Patent
Andersch et al.

(10) Patent No.: US 9,730,455 B2
(45) Date of Patent: Aug. 15, 2017

(54) COMPOSITION COMPRISING A BIOLOGICAL CONTROL AGENT AND AN INSECTICIDE

(71) Applicant: Bayer CropScience AG, Monheim (DE)

(72) Inventors: Wolfram Andersch, Bergisch Gladbach (DE); Wolfgang Thielert, Odenthal (DE); Bernd Springer, Cologne (DE); Peter Luth, Wismar (DE); Ute Eiben, Malchow/Poel (DE)

(73) Assignee: Bayer CropScience AG, Monheim (DE)

(*) Notice: Subject to any disclaimer, the term of this patent is extended or adjusted under 35 U.S.C. 154(b) by 0 days.

(21) Appl. No.: 14/646,547

(22) PCT Filed: Dec. 3, 2013

(86) PCT No.: PCT/EP2013/075321
§ 371 (c)(1),
(2) Date: May 21, 2015

(87) PCT Pub. No.: WO2014/086749
PCT Pub. Date: Jun. 12, 2014

(65) Prior Publication Data
US 2015/0296803 A1  Oct. 22, 2015

(30) Foreign Application Priority Data
Dec. 3, 2012 (EP) .................................. 12195202

(51) Int. Cl.
| | | |
|---|---|---|
| A01N 63/04 | (2006.01) | |
| A01N 47/40 | (2006.01) | |
| A01N 47/22 | (2006.01) | |
| A01N 43/56 | (2006.01) | |
| A01N 25/00 | (2006.01) | |
| A01N 51/00 | (2006.01) | |
| A01N 47/24 | (2006.01) | |
| A01N 43/22 | (2006.01) | |

(52) U.S. Cl.
CPC ............. *A01N 63/04* (2013.01); *A01N 25/00* (2013.01); *A01N 43/22* (2013.01); *A01N 43/56* (2013.01); *A01N 47/24* (2013.01); *A01N 47/40* (2013.01); *A01N 51/00* (2013.01)

(58) Field of Classification Search
CPC ........ A01N 63/04; A01N 47/22; A01N 47/40; A01N 43/22; A01N 43/78; A01N 25/00; A01N 43/56; A01N 51/00; A01N 47/24
See application file for complete search history.

(56) References Cited

U.S. PATENT DOCUMENTS

| | | | | |
|---|---|---|---|---|
| 5,989,543 | A * | 11/1999 | Davide | ..................... C12R 1/79 424/93.5 |
| 2011/0033436 | A1* | 2/2011 | Chen | ..................... A01N 63/00 424/93.461 |
| 2012/0201981 | A1* | 8/2012 | Becker | ..................... A01C 1/08 428/34.1 |

FOREIGN PATENT DOCUMENTS

| | | |
|---|---|---|
| CN | 102405939 A | 4/2012 |
| CN | 102422844 A | 4/2012 |
| WO | 91/02051 A1 | 2/1991 |
| WO | 94/25579 A2 | 11/1994 |
| WO | 96/21358 A1 | 7/1996 |
| WO | 2005/035486 A1 | 4/2005 |
| WO | 2009/116106 A1 | 9/2009 |
| WO | 2011/049233 A1 | 4/2011 |

OTHER PUBLICATIONS

NemOut WG Product Sheet, PROPHYTA Biologischer Pflanzenschutz GmbH, pp. 1-2.*
Ehteshamul-Haque, S., et al., "Effects of Pesticides on the Efficacy of Biocontrol Agents in the Control of Root Rot and Root Knot Disease Complex of Okra," Pakistan J. of Nematology, Pakistan Society of Nematologists, Jan. 1, 1995, vol. 13, No. 2, pp. 129-134.
Jacobs, et al., "Interactions Between Nematophagous Fungi and Consequences for Their Potential As Biological Agents for the Control of Potato Cyst nematodes," Mycological Research, Jan. 1, 2003, vol. 107, No. 1, pp. 47-56.
Oliveira, M. K. R. S., et al., "Controle Biologico De Fitonematoides Do Genero Pratylenchus Atraves De Inoculante Natural Em Cana-De-Acucar," Revista Brasileira de Ciencias Agrarias, Brazilian Journal of Agricultural Sciences, Jun. 7, 2011, vol. 6, No. 2, pp. 203-207.

(Continued)

*Primary Examiner* — John Pak
*Assistant Examiner* — Andriae M Holt
(74) *Attorney, Agent, or Firm* — Adam L. Lunceford; Michelle L. Samonek

(57) ABSTRACT

The present invention relates to a composition comprising at least one biological control agent selected from the group consisting of *Paecilomyces lilacinus* strain 251 (AGAL No. 89/030550) and *Coniothyrium minitans* CON/M/91-08 (DSM 9660) and/or a mutant of these strains having all the identifying characteristics of the respective strain, and/or at least one metabolite produced by the respective strain that exhibits activity against nematodes, insects and/or phytopathogens, and at least one insecticide (I) selected from the group consisting of acetylcholinesterase (AChE) inhibitors, nicotinic acetylcholine receptor (nAChR) agonists, nicotinic acetylcholine receptor (nAChR) allosteric activators, nicotinic acetylcholine receptor (nAChR) channel blockers and ryanodine receptor modulators in a synergistically effective amount. Furthermore, the present invention relates to a kit of parts comprising said composition and the use of said composition.

12 Claims, No Drawings

(56) References Cited

OTHER PUBLICATIONS

Pathan, M. A., et al., "Effect of Paecilomyces lilacinus and Furadan on Plant Growth, Root Nodulation and Reproduction of Meloidogyne incognita in Tomato," Pakistan J. of Nematology, Pakistan Society of Nematologists, 2005, vol. 23, No. 1, pp. 67-71.
Saikia, M. K., et al., "Integration of Carbofuran With Paecilomyces lilacinus for the Control of Root-Knot Nematode Meloidogyne incognita on Brinjal," Annals of Biology, Jun. 1, 2001, vol. 17, No. 1, pp. 79-82.
Sharma, H. K., et al., "Management of Meloidogyne incognita With Paecilomyces lilacinus and Neem Cake on Okra," Pesticide Research Journal, Dec. 2007, vol. 19, No. 2, pp. 166-168.
Vyas, R. V., et al., "Management of Root-Knoot Nematodes in Chickpea," Pakistan J. of Nematology, Pakistan Society of Nematologists, 1996, vol. 14, No. 2, pp. 117-119.
International Search Report and Written Opinion of the International Search Authority, International Application No. PCT/EP2013/075321, Jul. 16, 2014, 14 pages.
Colby, S.R., "Calculating Synergistic and Antagonistic Responses of Herbicide Combinations," Weeds, 1967, vol. 15 No. 1, pp. 20-22.
Kiewnick, S., et al., "Optimizing the efficacy of Paecilomyces lilacinus (strain 251) for the control of root-knot nematodes," Communications in Agricultural and Applied Biological Sciences, 2004, vol. 69, No. 3, pp. 373-380.
Mendoza, A., et al., "Efficacy of Pacilomyces lilacinus (strain 251) for the control of Radopholus similis in banana," Communications in Agricultural and Applied Biological Sciences, 2004, vol. 69, No. 3, pp. 365-372.

\* cited by examiner

COMPOSITION COMPRISING A BIOLOGICAL CONTROL AGENT AND AN INSECTICIDE

CROSS-REFERENCE TO RELATED APPLICATION(S)

The present application is a 35 U.S.C. §371 national stage entry of PCT/EP2013/075321, filed on Dec. 3, 2013, which claims priority of European Patent Application No. 12195202.2, filed on Dec. 3, 2012, which is hereby incorporated by reference in its entirety. Applicant claims priority to each of the foregoing patent applications. The PCT International Application was published in the English language.

The present invention relates to a composition comprising at least one biological control agent selected from specific microorganisms and/or a mutant of these strains having all the identifying characteristics of the respective strain, and/or at least one metabolite produced by the respective strain that exhibits activity against insects, nematodes and/or phytopathogens and at least one specified insecticide in a synergistically effective amount. Furthermore, the present invention relates to the use of this composition as well as a method for reducing overall damage of plants and plant parts.

Synthetic insecticides or fungicides often are non-specific and therefore can act on organisms other than the target ones, including other naturally occurring beneficial organisms. Because of their chemical nature, they may be also toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i. e. synthetic) pesticides. Thus, there is a need to manage food chain requirements while still allowing effective pest control.

A further problem arising with the use of synthetic insecticides or fungicides is that the repeated and exclusive application of an insecticide or fungicides often leads to selection of resistant microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The risk of resistance development in pathogen populations as well as environmental and human health concerns have fostered interest in identifying alternatives to synthetic insecticides and fungicides for managing plant diseases. The use of biological control agents (BCAs) is one alternative. However, the effectiveness of most BCAs is not at the same level as for conventional insecticides and fungicides, especially in case of severe infection pressure. Consequently, known biological control agents, their mutants and metabolites produced by them are, in particular in low application rates, not entirely satisfactory.

Thus, there is a constant need for developing new, alternative plant protection agents which in some areas at least help to fulfill the above-mentioned requirements.

*Paecilomyces lilacinus* strain 251 is known from WO 91/02051 as biological nematicide. It was found in 1979 and is approved for use as a nematicide e.g. in Bulgaria and Italy as well as in Belgium. The strain has been isolated from a Meloidogyne egg mass in Los Banos, Philippines (cf. WO 91/02051) and has been deposited with the Australian Government Analytical Laboratories (AGAL) in 1989 under the accession No. 89/030550.

WO 2009/116106 realtes to the strain *Trichoderma atroviride* SC1 which is effective for biocontrol of fungal diseases in plants. It has first been isolated from decayed hazelnut wood in northern Italy in 2000 and has been deposited at the "Centraalbureeau voor Schimmelcultures" under the deposition number CBS No. 122089 in 2007.

A further known biological control agent is the strain *Coniothyrium minitans* CON/M/91-08 (cf. WO 96/21358) which has been deposited under the number DSM 9660 with the German Collection of Microorganisms and Cell Cultures in Braunschweig. It is used as a biological control against the fungal pathogens *Sclerotinia sclerotiorum* and *Sclerotinia minor* (causal agents of white mold on many plant species).

In view of this, it was in particular an object of the present invention to provide compositions which exhibit activity against insects, mites, nematodes and/or phytopathogens. Moreover, it was a further particular object of the present invention, to reduce the application rates and broaden the activity spectrum of the biological control agents and insecticides, and thereby to provide a composition which, preferably at a reduced total amount of active compounds applied, has improved activity against insects, mites, nematodes and/or phytopathogens. In particular, it was a further object of the present invention to provide a composition which, when applied to a crop, results in a decreased amount of residues in the crop, thereby reducing the risk of resistance formation and nevertheless provides efficient disease control.

Accordingly, it was found that these objects at least partly are solved by the compositions according to the invention as defined in the following. The composition according to the present invention preferably fulfills the above-described needs. It has been surprisingly discovered that the application of the composition according to the present invention in a simultaneous or sequential way to plants, plant parts, harvested fruits, vegetables and/or plant's locus of growth preferably allows better control of insects, mites, nematodes and/or phytopathogens than it is possible with the strains, their mutants and/or their metabolites produced by the strains on the one hand and with the individual insecticides on the other hand, alone (synergistic mixtures). By applying the biological control agent and the insecticide according to the invention the activity against insects, mites, nematodes and/or phytopathogens is preferably increased in a superadditive manner.

As a consequence, the composition according to the present invention preferably allows a reduced total amount of active compounds to be used and thus the crops which have been treated by this composition preferably show a decreased amount of residues in the crop. Accordingly, the risk of resistance formation of harmful microorganisms is decreased.

The present invention is directed to a composition comprising at least one biological control agent selected from the group consisting of *Paecilomyces lilacinus* strain 251 (AGAL No. 89/030550), *Trichoderma atroviride* SC1 (CBS No. 122089), and *Coniothyrium minitans* CON/M/91-08 (DSM 9660) and/or a mutant of these strains having all the identifying characteristics of the respective strain, and/or at least one metabolite produced by the respective strain that exhibits activity against nematodes, insects and/or phytopathogens, and at least one insecticide (I) selected from the group consisting of acetylcholinesterase (AChE) inhibitors, nicotinic acetylcholine receptor (nAChR) agonists, nicotinic acetylcholine receptor (nAChR) allosteric activators, nicotinic acetylcholine receptor (nAChR) channel blockers and ryanodine receptor modulators in a synergistically effective amount.

Furthermore, the present invention relates to a kit of parts comprising at least one of the specific biological control agents and at least one insecticide (I). The present invention is further directed to the use of said composition for reducing overall damage of plants and plant parts as well as losses in harvested fruits or vegetables caused by insects, mites, nematodes and/or phytopathogens.

Moreover, the present invention provides a method for reducing overall damage of plants and plant parts as well as losses in harvested fruits or vegetables caused by insects, mites, nematodes and/or phytopathogens as well as a seed treated with the composition according to the present invention.

Biological Control Agents

In general "pesticidal" means the ability of a substance to increase mortality or inhibit the growth rate of plant pests. The term is used herein, to describe the property of a substance to exhibit activity against insects, mites, nematodes and/or phytopathogens. In the sense of the present invention the term "pests" include insects, mites, nematodes and/or phytopathogens.

As used herein, "biological control" is defined as control of a pathogen and/or insect and/or an acarid and/or a nematode by the use of a second organism. Known mechanisms of biological control include bacteria that control root rot by out-competing fungi for space or nutrients on the surface of the root. Bacterial toxins, such as antibiotics, have been used to control pathogens. The toxin can be isolated and applied directly to the plant or the bacterial species may be administered so it produces the toxin in situ. Other means of exerting biological control include the application of certain fungi producing ingredients active against a target phytopathogen, insect, mite or nematode, or attacking the target pest/pathogen. "biological control" as used in connection with the present invention may also encompass microorganisms having a beneficial effect on plant health, growth, vigor, stress response or yield. Application routes include spray application soil application and seed treatment.

The term "metabolite" refers to any compound, substance or byproduct of a fermentation of a said microorganism that has pesticidal activity.

The term "mutant" refers to a variant of the parental strain as well as methods for obtaining a mutant or variant in which the pesticidal activity is greater than that expressed by the parental strain. The "parent strain" is defined herein as the original strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art.

A "variant" is a strain having all the identifying characteristics of the respective Accession Numbers as indicated in this text and can be identified as having a genome that hybridizes under conditions of high stringency to the genome of the respective Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated Accession Number may also be defined as a strain having a genomic sequence that is greater than 85%, more preferably greater than 90% or more preferably greater than 95% sequence identity to the genome of the indicated Accession Number. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987) Supplement 30, section 7. 7. 18, Table 7. 7. 1.

AGAL is the abbreviation for "Australian Analytical Laboratories" which today is named "National Measurement Institute (NMI)" having the address 1, Suakin Street, Pymble NSW 2073, Australia.

CBS is the abbreviation for "Centraalbureau voor Schimmelcultures", an international depositary authority for the purposes of deposing microorganism strains under the Budapest treaty on the international recognition of the deposit of microorganisms for the purposes of patent procedure, having the address Uppsalalaan 8, 3584 CT Utrecht, Netherlands.

DMS is the abbreviation for "Deutsche Sammlung von Mikroorganismen and Zellkulturen GmbH" located at Inhoffenstr. 78 in 38124 Braunschweig, Germany.

The biological control agents used in the present invention are known in the art as follows:

Paecilomyces lilacinus Strain 251

Paecilomyces lilacinus, which was recently re-classified as *Prupureocillium lilacinum*, generally is a widely distributed saprophytic soil fungus which is readily isolatable throughout the world. *Paecilomyces lilacinus* strain 251 (in the following sometimes referred to as B1) has been shown to be effective under field conditions against plant pathogenic or rather parasitic nematodes which attack a variety of agriculturally important crops including banana, potato, pineapple, cotton, coffee, rice, black pepper, okra, avocado, tomato etc. (WO 91/02051). It is effective against many types of parasitic nematodes, including root knot (*Meloidogyne*), sting (*Belonolaimus*), burrowing (*Radopholus*), cyst (*Globodera* and *Heterodera*), root lesion (*Pratylenchus*) and other economically important nematodes species.

In general, the combination according to the invention is effective against nematodes of the species *Meloidogyne* such as the Southern Root-Knot nematode (*Meloidogyne incognita*), Javanese Root-Knot nematode (*Meloidogyne javanica*), Northern Root-Knot Nematode (*Meloidogyne hapla*) and Peanut Root-Knot Nematode (*Meloidogyne arenaria*); nematodes of the species *Ditylenchus* such as *Ditylenchus destructor* and *Ditylenchus dipsaci*; nematodes of the species *Pratylenchus* such as the Cob Root-Lesion Nematode (*Pratylenchus penetrans*), Chrysanthemum Root-Lesion Nematode (*Pratylenchus fallax*), *Pratylenchus cof-* feae, Pratylenchus loosi and Walnut Root-Lesion Nematode (Pratylenchus vulnus); Nematodes of the species Globodera such as Globodera rostochiensis and Globodera pallida; Nematodes of the species Heterodera such as Heterodera glycines Heterodera schachtii; Nematodes of the species Aphelenchoides such as the Rice White-tip Nematode (Aphelenchoides besseyi), Aphelenchoides ritzemabosi and Aphelenchoides fragariae; Nematodes of the species Aphelenchus such as Aphelenchus avenae; Nematodes of the species Radopholus, such as the Burrowing-Nematode (Radopholus similis); Nematodes of the species Tylenchulus such as Tylenchulus semipenetrans; Nematodes of the species Rotylenchulus such as Rotylenchulus reniformis; Nematodes living in trees such as Bursaphelenchus xylophilus and the Red Ring Nematode (Bursaphelenchus cocophilus) etc.

Exemplary commercial products containing Paecilomyces lilacinus strain 251 are BioAct® WG and MeloCon WG. The activity of Paecilomyces lilacinus strain 251 is described inter alia in A. Khan et al., FEMS Microbiology Letters, 227, 107-111, 2003 and S. Kiewnick at al. Biological Control 38, 179-187, 2006. Its isolation and characteristic properties are disclosed in WO 91/02051, which is incorporated herein by reference. The strain has been deposited with the Australian Government Analytical Laboratories (AGAL) in 1989 under the accession No. 89/030550.

Paecilomyces lilacinus strain 251 of the invention is known and can be cultivated and caused to sporulate using methods well known in the art as described e.g. in WO 91/02051. Harvesting of spores is preferably performed under conditions that do not promote heat, including shaking, scraping, washing and centrifugation. The spore material is then dried by a suitable process such as air drying, freeze drying or desiccation with a suitable desiccant and can be reformulated by addition of inert filler or new growth material to provide a suitable number of spores per unit amount of product.

Usually the strain is formulated on a carrier, preferably a water-soluble sugar carrier, in a concentration of between $1 \times 10^5$ and about $1 \times 10^{10}$ spores/g of carrier, preferably between $5 \times 10^7$ and about $5 \times 10^9$ spores/g carrier. However, also formulations up to about $1 \times 10^{10}$ spores/g, about $2 \times 10^{10}$ spores/g, about $5 \times 10^{10}$ spores/g, about $1 \times 10^{11}$ spores/g or even about $2 \times 10^{11}$ spores/g or about $3 \times 10^{11}$ spores/g may be obtained. The carrier may e.g. be selected from polysaccharides or crude plant products such as cornmeal to assist fungal growth. Likewise whole seeds such as wheat or sesame may be used to present the fungus. Mineral matter such as silica and vermiculite may also be added. Paecilomyces lilacinus strain 251 may be formulated as a powder or in pelleted form. In this case the carrier is preferably formulated so that slow release of the spores is obtained over a considerable period of time following application. The infective propagules of Paecilomyces lilacinus strain 251 may be applied to the crop either in liquid suspension, optionally in association with a suitable nematicidal carrier or, less preferred, as solid formulation, and in association with a suitable excipient.

The final dosage of infective propagules of Paecilomyces lilacinus starin 251 is normally in the order of between 1× about $10^5$ and about $1 \times 10^7$, preferably between about $1 \times 10^5$ and about $1 \times 10^6$ spores per gram of soil for nursery applications and for field applications.

It may be applied to crops using any of the methods well known in the art. It may be advantageous to apply the inventive composition to the environment of the roots so minimizing the root damage caused by nematodes. This may be achieved by coating of the seeds with the inventive composition so that emergence of roots results in a fungal inoculum in their environment; by dipping or spraying the root regions of seedlings or seed trays in a nursery situation, or by application of the composition at the site of planting, either in aqueous suspension or in solid form. It is particularly preferred that the inventive composition is specifically applied to the regions of the plant rhizosphere affected by nematodes. The composition may be applied as a soil drench or through drip (trickle) or sprinkler (microjet) irrigation system. Vegetables and other transplants can be treated just before transplanting with a soil drench to protect from nematodes entering the developing root ball in the field. Nonfumigated field soils should be treated with the composition two weeks before seeding or transplanting to reduce initial nematode infestation. Application can then be repeated e.g. at 6 weeks intervals.

The spores of Paecilomyces lilacinus strain 251 germinate upon contact with nematode eggs, juvenile stages and adults in the soil. The growing fungus engulfs and penetrates the nematode over a period of several days, killing it by consuming its body contents.

Paecilomyces lilacinus strain 251 is an obligate parasite of nematodes; it does not colonize the root or feed on root exudates. In the absence of nematodes, spores of Paecilomyces lilacinus strain 251 decline in the soil over a period of 3 to 6 weeks at a rate depending on soil type and temperature.

According to the invention Paecilomyces lilacinus strain 251 encompasses mutants having all identifying characteristics of the respective strain, and/or at least one metabolite produced by the respective strain that exhibits activity against nematodes and/or insects.

Trichoderma atroviride SC1

Trichoderma is a cosmopolitan fungal genus, which can colonize soils, rhizospheres and phyllospheres. Trichoderma species are frequently found on decaying wood and vegetable material. Several Trichoderma strains are economically important producers of industrial enzymes. Some Trichoderma strains have already been used as biocontrol agents against numerous plant pathogens and quite a few have been developed for use as commercial (i.e. Trichoderma harzianum, known as Trichodex® or Trianum®, Trichoderma virens, known as SoilGard®, and Trichoderma atroviride, known as Esquive®) biocontrol products for field and greenhouse crops.

Trichoderma atroviride SC1 (in the following sometimes referred to as B2) is known to suppress and to prevent the development of plant pathogens, in particular fruits and root rots, such as those caused by Botrytis cinerea and Armillaria spp., powdery mildews and wood diseases (Esca disease) (WO2009/116106 which is incorporated herein by reference). It is deposited under the accession number CBS No. 122089.

As most Trichoderma spp., Trichoderma atroviride SC1 is a mesophilic fungus and able to utilize a wide range of compounds as carbon and nitrogen sources. Accordingly, it persists in soil at effective levels for long periods (more than one year).

However, fungal growth in culture media is superior with the addition of some nitrogen sources such as yeast extract, nitrite, tryptone, peptone, glutamine and asparagine or some carbon sources such as mannose, galactose, sucrose, malt extract, cellobiose glucose and threalose. For the preparation of Trichoderma atroviride SC1 compositions the spores are cultured by methods known to those skilled in the art. For example it can be effected by inoculation of Trichoderma atroviride SC1 on a common nutrient substrate in liquid suspension or on solid substrate to obtain preferably at least $10^2$-$10^3$ conidia/(ml or g) (active concentration), preferably about $1\times10^4$ to about $1\times10^8$ conidia/(ml or g) which are then used in a composition preferably comprising an effective amount of this strain in a quantity of at least $10^2$-$10^3$ conidia/(ml or g), preferably about $1\times10^4$ $1\times10^8$ conidia/(ml or g). Other cultivation methods are disclosed in WO2009/116106.

For soil applications a final concentration of conidia in the soil of between about $1\times10^2$ and about $1\times10^5$ spores/(ml or g) soil is envisaged. Upon foliar application, the amount applied ranges between about $1\times10^{11}$ and about $1\times10^{13}$ spores/hectare, preferably about $1\times10^{12}$ spores/hectare.

Plant treatment and/or prevention is carried out by using *Trichoderma atroviride* SC1 cultures grown in liquid or semi-solid media or on a solid substrate and by applying this suspension onto parts of the plant or applying the enriched substrate on or into the sol in close proximity of the plant in need of such a treatment. The treatment can be affected by applying agricultural compositions to plants, on the leaves of plants, on wounds made during cutting or pruning, or to the sol to suppress the development of fungal diseases on roots. The treatment can be carried out during plant vegetative period or during dormancy. The treatment can be applied once (i. e. at planting time in soil) or repeatedly as needed.

According to the invention *Trichoderma atroviride* SC1 encompasses mutants having all identifying characteristics of the respective strain, and/or at least one metabolite produced by the respective strain that exhibits activity against pathogenic fungi.

*Coniothyrium minitans* Strain CON/M/91-08

The naturally occurring fungus *Coniothyrium minitans* has been first identified in 1947 and can be found in soils world-wide. It attacks and destroys the sclerotia (overwintering or survival structures) of *Sclerotinia sclerotiorum*, *Sclerotinia minor*, other *Sclerotinia* species and *Sclerotium cepivorum*. These pathogens have a wide host range of several hundered species of plants (including many vegetables and ornamentals). They commonly cause white mold on cole crops and beans, and are occasionally found on tomatoes and peppers. Additionally, they cause leaf drop on lettuce and white mold in carrots. Normally, these sclerotia will germinate in the spring and summer, producing spores that infect many crops, enabling white mold disease to develop. The strain *Coniothyrum minitans* strain CON/M/91-08 (in the following sometimes referred to as B3) is commercially available as Contans®.

*Coniothyrium minitans* strain CON/M/91-08 can be cultured as described in WO 96/21358 which is incorporated herein by reference. For example this strain can be cultured on suitable substrates, such as seeds of grain, bran, straw or other plant materials, or also with the help of agar culture media that are customary in mycology, such as potato dextrose agar, or malt peptone agar, or on suitable support materials to which a culture medium has been added, as well as in liquid nutrient media without the addition of agar.

Usually the strain is formulated on a carrier, preferably a water-soluble sugar carrier, in a concentration of between $1\times10^9$ and about $1\times10^{15}$ spores/g of carrier, preferably between $1\times10^{10}$ and about $1\times10^{13}$ spores/g carrier. Most preferably, the concentration lies between about $1\times10^8$ and about $1\times10^{10}$ spores/g of carrier, such as at about $1\times10^9$ spores/g carrier. In particular the water-soluble sugar is glucose.

According to the invention *Coniothyrium minitans* strain CON/M/91-08 encompasses mutants having all identifying characteristics of the respective strain, and/or at least one metabolite produced by the respective strain that exhibits activity against *Sclerotinia* spp., such as *Sclerotinia sclerotiorum* and/or *Sclerotinia minor* and/or *Sclerotium cepivorum*.

According to one embodiment of the present invention the biological control agent comprises not only the isolated, pure cultures of the respective microorganisms, but also their suspensions in a whole broth culture or a metabolite-containing supernatant or a purified metabolite obtained from whole broth culture of the strain. "Whole broth culture" refers to a liquid culture containing both cells and media. "Supernatant" refers to the liquid broth remaining when cells grown in broth are removed by centrifugation, filtration, sedimentation, or other means well known in the art.

The above-mentioned metabolites produced by the non-pathogenic microorganisms include antibiotics, enzymes, siderophores and growth promoting agents.

According to the invention, the biological control agent may be employed or used in any physiologic state such as active or dormant.

Preferably, the biological control agent is *Paecilomyces lilacinus* strain 251 (AGAL No. 89/030550), and/or a mutant of this strain having all the identifying characteristics of this strain, and/or at least one metabolite produced by this strain that exhibits activity against nematodes, insects and/or phytopathogens. In particular, this strain, its mutant and/or metabolite as defined above is preferred in case of the seed treatment and the seed treated with the composition according to the present invention. In another preferred embodiment, the strain, its mutant and/or metabolite as defined above is used in soil or foliar applications.

Insecticides

"Insecticides" as well as the term "insecticidal" refers to the ability of a substance to increase mortality or inhibit growth rate of insects. As used herein, the term "insects" includes all organisms in the class "Insecta". The term "pre-adult" insects refers to any form of an organism prior to the adult stage, including, for example, eggs, larvae, and nymphs.

"Nematicides" and "nematicidal" refers to the ability of a substance to increase mortality or inhibit the growth rate of nematodes. In general, the term "nematode" comprises eggs, larvae, juvenile and mature forms of said organism.

"Acaricide" and "acaricidal" refers to the ability of a substance to increase mortality or inhibit growth rate of ectoparasites belonging to the class Arachnida, sub-class Acari.

The active ingredients specified herein by their "common name" are known and described, for example, in the Pesticide Manual ("The Pesticide Manual", 14th Ed., British Crop Protection Council 2006) or can be searched in the internet.

The term "at least one" indicates that in any case a substance as specified, such as a metabolite or an insecticide, is present in the composition according to the invention. However, more than one such as (at least) two, (at least) three, (at least) four, (at least) 5 or even more such substances may be present in the composition according to the invention.

Insecticide (I)

According to the invention, the at least one insecticide (I) is selected from the group consisting of acetylcholinesterase (AChE) inhibitors, nicotinic acetylcholine receptor (nAChR) agonists, nicotinic acetylcholine receptor (nAChR) allosteric activators, nicotinic acetylcholine receptor (nAChR) channel blockers and ryanodine receptor modulators.

Preferably, the acetylcholinesterase (AChE) inhibitor is selected from the group consisting of carbamates and organophosphates. Still preferably, the nicotinic acetylcholine receptor (nAChR) agonist is a neonicotinoid. Still preferably, the nicotinic acetylcholine receptor (nAChR) allosteric activator is a spinosyns. Still preferably, the ryanodine receptor modulator is a diamide.

In a preferred embodiment the acetylcholinesterase (AChE) inhibitor is selected from the group consisting of carbamates, e.g. Alanycarb (I1), Aldicarb (I2), Bendiocarb (I3), Benfuracarb (I4), Butocarboxim (I5), Butoxycarboxim (I6), Carbaryl (I7), Carbofuran (I8), Carbosulfan (I9), Ethiofencarb (I10), Fenobucarb (I11), Formetanate (I12), Furathiocarb (I13), lsoprocarb (I14), Methiocarb (I15), Methomyl (I16), Metolcarb (I17), Oxamyl (I18), Pirimicarb (I19), Propoxur (I20), Thiodicarb (I21), Thiofanox (I22), Triazamate (I23), Trimethacarb (I24), XMC (I25), and Xylylcarb (I26); or organophosphates, e.g. Acephate (I27), Azamethiphos (I28), Azinphos-ethyl (I29), Azinphos-methyl (I30), Cadusafos (I31), Chlorethoxyfos (I32), Chlorfenvinphos (I33), Chlormephos (I34), Chlorpyrifos (I35), Chlorpyrifos-methyl (I36), Coumaphos (I37), Cyanophos (I38), Demeton-S-methyl (I39), Diazinon (I40), Dichlorvos/DDVP (I41), Dicrotophos (I42), Dimethoate (I43), Dimethylvinphos (I44), Disulfoton (I45), EPN (I46), Ethion (I47), Ethoprophos (I48), Famphur (I49), Fenamiphos (I50), Fenitrothion (I51), Fenthion (I52), Fosthiazate (I53), Heptenophos (I54), Imicyafos (I55), lsofenphos (I56), Isopropyl O-(methoxyaminothio-phosphoryl) salicylate (I57), Isoxathion (I58), Malathion (I59), Mecarbam (I60), Methamidophos (I61), Methidathion (I62), Mevinphos (I63), Monocrotophos (I64), Naled (I65), Omethoate (I66), Oxydemeton-methyl (I67), Parathion (I68), Parathion-methyl (I69), Phenthoate (I70), Phorate (I71), Phosalone (I72), Phosmet (I73), Phosphamidon (I74), Phoxim (I75), Pirimiphos-methyl (I76), Profenofos (I77), Propetamphos (I78), Prothiofos (I79), Pyraclofos (I80), Pyridaphenthion (I81), Quinalphos (I82), Sulfotep (I83), Tebupirimfos (I84), Temephos (I85), Terbufos (I86), Tetrachlorvinphos (I87), Thiometon (I88), Triazophos (I89), Trichlorfon (I90), and Vamidothion (I91).

In another preferred embodiment the nicotinic acetylcholine receptor (nAChR) agonist is selected from the group consisting of Acetamiprid (I141), Clothianidin (I142), Dinotefuran (I143), Imidacloprid (I144), Nitenpyram (I145), Thiacloprid (I146), and Thiamethoxam (I147); or Nicotine (I148); or Sulfoxaflor (I149).

In another preferred embodiment the nicotinic acetylcholine receptor (nAChR) allosteric activator is selected from the group consisting of Spinetoram (I150) and Spinosad (I151).

Still in another preferred embodiment the nicotinic acetylcholine receptor (nAChR) channel blocker is selected from the group consisting of Bensultap (I187), Cartap hydrochloride (I188), Thiocyclam (I189), and Thiosultap-sodium (I190).

Still in another preferred embodiment the ryanodine receptor modulator is selected form the group consisting of Chlorantraniliprole (I231), Cyantraniliprole (I232), and Flubendiamide (I233).

In a preferred embodiment the insecticide (I) is selected from the group consisting of Carbofuran (I8), Methiocarb (I15), Thiodicarb (I21), Acephate (I27), Chlorpyrifos (I35), Profenofos (I77), Acetamiprid (I141), Clothianidin (I142), Dinotefuran (I143), Imidacloprid (I144), Thiacloprid (I146), Thiamethoxam (I147), Sulfoxaflor (I149), Spinetoram (I150), Spinosad (I151), Chlorantraniliprole (I231), Cyantraniliprole (I232), and Flubendiamide (I233).

In one embodiment of the present invention, the insecticide (I), e.g., the insecticide (I) for use in seed treatment, is selected from the group consisting of Carbofuran (I8), Methiocarb (I15), Thiodicarb (I21), Clothianidin (I142), Imidacloprid (I144), Thiamethoxam (I147), Sulfoxaflor (I149) and Spinosad (I151).

In one embodiment of the present invention, the insecticide (I), e.g., the insecticide (I) for use in seed treatment, foliar or soil application is selected from the group consisting of Cyantraniliprole (I232), Chlorantraniliprole (I231), Methiocarb (I15), Spinetoram (I150), Spinosad (I151), Thiodicarb (I21), Clothianidin (I142), Thiacloprid (I146) and Thiamethoxam (I147).

Compositions According to the Present Invention

According to the present invention the composition comprises at least one biological control agent selected from the group consisting of *Paecilomyces lilacinus* strain 251 (AGAL No. 89/030550), *Trichoderma atroviride* SC1 (CBS No. 122089), and *Coniothyrium minitans* CON/M/91-08 (DSM 9660) and/or a mutant of these strains having all the identifying characteristics of the respective strain, and/or at least one metabolite produced by the respective strain that exhibits activity against nematodes, insects and/or phytopathogens, and at least one insecticide (I) selected from the group consisting of acetylcholinesterase (AChE) inhibitors, nicotinic acetylcholine receptor (nAChR) agonists, nicotinic acetylcholine receptor (nAChR) allosteric activators, nicotinic acetylcholine receptor (nAChR) channel blockers and ryanodine receptor modulators in a synergistically effective amount.

A "synergistically effective amount" according to the present invention represents a quantity of a combination of a biological control agent and an insecticide that is statistically significantly more effective against insects, mites, nematodes and/or phytopathogens than the biological control agent or the insecticide only.

In a preferred embodiment the composition according to the present invention comprises the following combinations:
B1+I1, B1+I2, B1+I3, B1+I4, B1+I5, B1+I6, B1+I7, B1+I8, B1+I9, B1+I10, B1+I11, B1+I12, B1+I13, B1+I14, B1+I15, B1+I16, B1+I17, B1+I18, B1+I19, B1+I20, B1+I21, B1+I22, B1+I23, B1+I24, B1+I25, B1+I26, B1+I27, B1+I28, B1+I29, B1+I30, B1+I31, B1+I32, B1+I33, B1+I34, B1+I35, B1+I36, B1+I37, B1+I38, B1+I39, B1+I40, B1+I41, B1+I42, B1+I43, B1+I44, B1+I45, B1+I46, B1+I47, B1+I48, B1+I49, B1+I50, B1+I51, B1+I52, B1+I53, B1+I54, B1+I55, B1+I56, B1+I57, B1+I58, B1+I59, B1+I60, B1+I61, B1+I62, B1+I63, B1+I64, B1+I65, B1+I66, B1+I67, B1+I68, B1+I69, B1+I70, B1+I71, B1+I72, B1+I73, B1+I74, B1+I75, B1+I76, B1+I77, B1+I78, B1+I79, B1+I80, B1+I81, B1+I82, B1+I83, B1+I84, B1+I85, B1+I86, B1+I87, B1+I88, B1+I89, B1+I90, B1+I91, B1+I141, B1+I142, B1+I143, B1+I144, B1+I145, B1+I146, B1+I147, B1+I148, B1+I149, B1+I150, B1+I151, B1+I187, B1+I188, B1+I189, B1+I190, B1+I231, B1+I232, B1+I233;
B2+I1, B2+I2, B2+I3, B2+I4, B2+I5, B2+I6, B2+I7, B2+I8, B2+I9, B2+B20, B2+I11, B2+I12, B2+I13, B2+I14, B2+I15, B2+I16, B2+I17, B2+I18, B2+I19, B2+I20, B2+I21, B2+I22, B2+I23, B2+I24, B2+I25, B2+I26, B2+I27, B2+I28, B2+I29, B2+I30, B2+I31, B2+I32, B2+I33, B2+I34, B2+I35, B2+I36, B2+I37, B2+I38, B2+I39, B2+I40, B2+I41, B2+I42, B2+I43, B2+I44, B2+I45, B2+I46, B2+I47, B2+I48, B2+I49, B2+I50, B2+I51, B2+I52, B2+I53, B2+I54, B2+I55, B2+I56, B2+I57, B2+I58, B2+I59, B2+I60, B2+I61, B2+I62, B2+I63, B2+I64, B2+I65, B2+I66, B2+I67, B2+I68, B2+I69, B2+I70, B2+I71, B2+I72, B2+I73, B2+I74, B2+I75, B2+I76, B2+I77, B2+I78, B2+I79, B2+I80, B2+I81, B2+I82, B2+I83, B2+I84, B2+I85, B2+I86, B2+I87, B2+I88, B2+I89, B2+I90, B2+I91, B2+I141, B2+I142, B2+I143, B2+I144, B2+I145, B2+I146, B2+I147, B2+I148, B2+I149, B2+I150, B2+I151, B2+I187, B2+I188, B2+I189, B2+I190, B2+I231, B2+I232, B2+I233; B3+I1, B3+I2, B3+I3, B3+I4, B3+I5, B3+I6, B3+I7, B3+I8, B3+I9, B3+B30, B3+I11, B3+I12, B3+I13, B3+I14, B3+I15, B3+I16, B3+I17, B3+I18, B3+I19, B3+I20, B3+I21, B3+I22, B3+I23, B3+I24, B3+I25, B3+I26, B3+I27, B3+I28, B3+I29, B3+I30, B3+I31, B3+I32, B3+I33, B3+I34, B3+I35, B3+I36, B3+I37, B3+I38, B3+I39, B3+I40, B3+I41, B3+I42, B3+I43, B3+I44, B3+I45, B3+I46, B3+I47, B3+I48, B3+I49, B3+I50, B3+I51, B3+I52, B3+I53, B3+I54, B3+I55, B3+I56, B3+I57, B3+I58, B3+I59, B3+I60, B3+I61, B3+I62, B3+I63, B3+I64, B3+I65, B3+I66, B3+I67, B3+I68, B3+I69, B3+I70, B3+I71, B3+I72, B3+I73, B3+I74, B3+I75, B3+I76, B3+I77, B3+I78, B3+I79, B3+I80, B3+I81, B3+I82, B3+I83, B3+I84, B3+I85, B3+I86, B3+I87, B3+I88, B3+I89, B3+I90, B3+I91, B3+I141, B3+I142, B3+I143, B3+I144, B3+I145, B3+I146, B3+I147, B3+I148, B3+I149, B3+I150, B3+I151, B3+I187, B3+I188, B3+I189, B3+I190, B3+I231, B3+I232, B3+I233.

In another preferred embodiment the composition according to the present invention comprises the following combinations:
B1+I1, B1+I2, B1+I3, B1+I4, B1+I5, B1+I6, B1+I7, B1+I8, B1+I9, B1+B10, B1+I11, B1+I12, B1+I13, B1+I14, B1+I15, B1+I16, B1+I17, B1+I18, B1+I19, B1+I20, B1+I21, B1+I22, B1+I23, B1+I24, B1+I25, B1+I26, B1+I27, B1+I28, B1+I29, B1+I30, B1+I31, B1+I32, B1+I33, B1+I34, B1+I35, B1+I36, B1+I37, B1+I38, B1+I39, B1+I40, B1+I41, B1+I42, B1+I43, B1+I44, B1+I45, B1+I46, B1+I47, B1+I48, B1+I49, B1+I50, B1+I51, B1+I52, B1+I53, B1+I54, B1+I55, B1+I56, B1+I57, B1+I58, B1+I59, B1+I60, B1+I61, B1+I62, B1+I63, B1+I64, B1+I65, B1+I66, B1+I67, B1+I68, B1+I69, B1+I70, B1+I71, B1+I72, B1+I73, B1+I74, B1+I75, B1+I76, B1+I77, B1+I78, B1+I79, B1+I80, B1+I81, B1+I82, B1+I83, B1+I84, B1+I85, B1+I86, B1+I87, B1+I88, B1+I89, B1+I90, B1+I91, B1+I141, B1+I142, B1+I143, B1+I144, B1+I145, B1+I146, B1+I147, B1+I148, B1+I149, B1+I150, B1+I151, B1+I187, B1+I188, B1+I189, B1+I190, B1+I231, B1+I232, B1+I233.

In a highly preferred embodiment the present invention relates to a composition comprising the following combinations:
B1+I8, B1+I15, B1+I21, B1+I27, B1+I35, B1+I77, B1+I141, B1+I142, B1+I143, B1+I144, B1+I146, B1+I147, B1+I149, B1+I150, B1+I151, B1+I231, B1+I232, B1+I233; B2+I8, B2+I15, B2+I21, B2+I27, B2+I35, B2+I77, B2+I141, B2+I142, B2+I143, B2+I144, B2+I146, B2+I147, B2+I149, B2+I150, B2+I151, B2+I231, B2+I232, B2+I233; B3+I8, B3+I15, B3+I21, B3+I27, B3+I35, B3+I77, B3+I141, B3+I142, B3+I143, B3+I144, B3+I146, B3+I147, B3+I149, B3+I150, B3+I151, B3+I231, B3+I232, B3+I233.

In another highly preferred embodiment the present invention relates to a composition comprising the following combinations:
B1+I8, B1+I15, B1+I21, B1+I27, B1+I35, B1+I77, B1+I141, B1+I142, B1+I143, B1+I144, B1+I146, B1+I147, B1+I149, B1+I150, B1+I151, B1+I231, B1+I232, B1+I233.

In one embodiment of the present invention, the composition used in seed treatment, comprises the following combinations:
B1+I8, B1+I15, B1+I21, B1+I142, B1+B144, B1+I147, B1+I149, B1+I151.

In another embodiment, the composition used for foliar or soil applications comprises the following combinations:
B1+I232, B1+I231, B1+I15, B1+I150, B1+I151, B1+I21, B1+I142, B1+I146 and B1+I147;
B3+I1232, B3+I231, B3+I150, B3+I21 and B3+I146.

In a preferred embodiment the composition according the present invention further comprising at least one additional insecticide (II) and/or at least one fungicide, with the proviso that insecticide (II) is not identical to insecticide (I) and the biological control agent is not identical to the fungicide.

Insecticide (II)

Insecticide (II) differs from insecticide (I). In a preferred embodiment of the present invention the insecticide (II) is a synthetic insecticide. As used herein, the term "synthetic" defines a compound that has not been obtained from a biological control agent. Especially a synthetic insecticide or fungicide is no metabolite of the biological control agents according to the present invention.

According to one embodiment of the present invention preferred insecticides are selected from the group consisting of
(1) Acetylcholinesterase (AChE) inhibitors, for example carbamates, e.g. Alanycarb (I1), Aldicarb (I2), Bendiocarb (I3), Benfuracarb (I4), Butocarboxim (I5), Butoxycarboxim (I6), Carbaryl (I7), Carbofuran (I8), Carbosulfan (I9), Ethiofencarb (I10), Fenobucarb (I11), Formetanate (I12), Furathiocarb (I13), lsoprocarb (I14), Methiocarb (I15), Methomyl (I16), Metolcarb (I17), Oxamyl (I18), Pirimicarb (I19), Propoxur (I20), Thiodicarb (I21), Thiofanox (I22), Triazamate (I23), Trimethacarb (I24), XMC (I25), and Xylylcarb (I26); or
organophosphates, e.g. Acephate (I27), Azamethiphos (I28), Azinphos-ethyl (I29), Azinphos-methyl (I30), Cadusafos (I31), Chlorethoxyfos (I32), Chlorfenvinphos (I33), Chlormephos (I34), Chlorpyrifos (I35), Chlorpyrifos-methyl (I36), Coumaphos (I37), Cyanophos (I38), Demeton-S-methyl (I39), Diazinon (I40), Dichlorvos/DDVP (I41), Dicrotophos (I42), Dimethoate (I43), Dimethylvinphos (I44), Disulfoton (I45), EPN (I46), Ethion (I47), Ethoprophos (I48), Famphur (I49), Fenamiphos (I50), Fenitrothion (I51), Fenthion (I52), Fosthiazate (I53), Heptenophos (I54), Imicyafos (I55), lsofenphos (I56), Isopropyl O-(methoxyaminothio-phosphoryl) salicylate (I57), Isoxathion (I58), Malathion (I59), Mecarbam (I60), Methamidophos (I61), Methidathion (I62), Mevinphos (I63), Monocrotophos (I64), Naled (I65), Omethoate (I66), Oxydemeton-methyl (I67), Parathion (I68), Parathion-methyl (I69), Phenthoate (I70), Phorate (I71), Phosalone (I72), Phosmet (I73), Phosphamidon (I74), Phoxim (I75), Pirimiphos-methyl (I76), Profenofos (I77), Propetamphos (I78), Prothiofos (I79), Pyraclofos (I80), Pyridaphenthion (I81), Quinalphos (I82), Sulfotep (I83), Tebupirimfos (I84), Temephos (I85), Terbufos (I86), Tetrachlorvinphos (I87), Thiometon (I88), Triazophos (I89), Trichlorfon (I90), and Vamidothion (I91);
(2) GABA-gated chloride channel antagonists, for example cyclodiene organochlorines, e.g. Chlordane (I92) and Endosulfan (I93); or phenylpyrazoles (fiproles), e.g. Ethiprole (I94) and Fipronil (I95);

(3) Sodium channel modulators/voltage-dependent sodium channel blockers, for example pyrethroids, e.g. Acrinathrin (I96), Allethrin (I97), d-cis-trans Allethrin (I98), d-trans Allethrin (I99), Bifenthrin (I100), Bioallethrin (I101), Bioallethrin S-cyclopentenyl isomer (I102), Bioresmethrin (I103), Cycloprothrin (I104), Cyfluthrin (I105), beta-Cyfluthrin (I106), Cyhalothrin (I107), lambda-Cyhalothrin (I108), gamma-Cyhalothrin (I109), Cypermethrin (I110), alpha-Cypermethrin (I111), beta-Cypermethrin (I112), theta-Cypermethrin (I113), zeta-Cypermethrin (I114), Cyphenothrin [(1R)-trans isomers] (I115), Deltamethrin (I116), Empenthrin [(EZ)-(1R) isomers) (I117), Esfenvalerate (I118), Etofenprox (I119), Fenpropathrin (I120), Fenvalerate (I121), Flucythrinate (I122), Flumethrin (I123), tau-Fluvalinate (I124), Halfenprox (I125), lmiprothrin (I126), Kadethrin (I127), Permethrin (I128), Phenothrin [(1R)-trans isomer) (I129), Prallethrin (I130), Pyrethrine (pyrethrum) (I131), Resmethrin (I132), Silafluofen (I133), Tefluthrin (I134), Tetramethrin (I135), Tetramethrin [(1R) isomers)] (I136), Tralomethrin (I137), and Transfluthrin (I138); or DDT (I139); or Methoxychlor (I140);

(4) Nicotinic acetylcholine receptor (nAChR) agonists, for example neonicotinoids, e.g. Acetamiprid (I141), Clothianidin (I142), Dinotefuran (I143), Imidacloprid (I144), Nitenpyram (I145), Thiacloprid (I146), and Thiamethoxam (I147); or Nicotine (I148); or Sulfoxaflor (I149).

(5) Nicotinic acetylcholine receptor (nAChR) allosteric activators, for example spinosyns, e.g. Spinetoram (I150) and Spinosad (I151);

(6) Chloride channel activators, for example avermectins/milbemycins, e.g. Abamectin (I152), Emamectin benzoate (I153), Lepimectin (I154), and Milbemectin (I155);

(7) Juvenile hormone mimics, for example juvenile hormon analogues, e.g. Hydroprene (I156), Kinoprene (I157), and Methoprene (I158); or Fenoxycarb (I159); or Pyriproxyfen (I160);

(8) Miscellaneous non-specific (multi-site) inhibitors, for example alkyl halides, e.g. Methyl bromide (I161) and other alkyl halides; or Chloropicrin (I162); or Sulfuryl fluoride (I163); or Borax (I164); or Tartar emetic (I165);

(9) Selective homopteran feeding blockers, e.g. Pymetrozine (I166); or Flonicamid (I167);

(10) Mite growth inhibitors, e.g. Clofentezine (I168), Hexythiazox (I169), and Diflovidazin (I170); or Etoxazole (I171);

(11) Microbial disruptors of insect midgut membranes, e.g.
Bacillus thuringiensis subspecies *israelensis* (I172), Bacillus thuringiensis subspecies *aizawai* (I173), Bacillus thuringiensis subspecies *kurstaki* (I174), Bacillus thuringiensis subspecies *tenebrionis* (I175), and B.t. crop proteins: Cry1Ab, Cry1Ac, Cry1Fa, Cry1A.105, Cry2Ab, Vip3A, mCry3A, Cry3Ab, Cry3Bb, Cry34 Ab1/35Ab1 (I176); or Bacillus sphaericus (I177);

(12) Inhibitors of mitochondrial ATP synthase, for example Diafenthiuron (I178); or organotin miticides, e.g. Azocyclotin (I179), Cyhexatin (I180), and Fenbutatin oxide (I181); or Propargite (I182); or Tetradifon (I183);

(13) Uncouplers of oxidative phoshorylation via disruption of the proton gradient, for example Chlorfenapyr (I184), DNOC (I185), and Sulfluramid (I186);

(14) Nicotinic acetylcholine receptor (nAChR) channel blockers, for example Bensultap (I187), Cartap hydrochloride (I188), Thiocyclam (I189), and Thiosultap-sodium (I190);

(15) Inhibitors of chitin biosynthesis, type 0, for example Bistrifluron (I191), Chlorfluazuron (I192), Diflubenzuron (I193), Flucycloxuron (I194), Flufenoxuron (I195), Hexaflumuron (I196), Lufenuron (I197), Novaluron (I198), Noviflumuron (I199), Teflubenzuron (I200), and Triflumuron (I201);

(16) Inhibitors of chitin biosynthesis, type 1, for example Buprofezin (I202);

(17) Moulting disruptors, for example Cyromazine (I203);

(18) Ecdysone receptor agonists, for example Chromafenozide (I204), Halofenozide (I205), Methoxyfenozide (I206), and Tebufenozide (I207);

(19) Octopamine receptor agonists, for example Amitraz (I208);

(20) Mitochondrial complex III electron transport inhibitors, for example Hydramethylnon (I209); or Acequinocyl (I210); or Fluacrypyrim (I211);

(21) Mitochondrial complex I electron transport inhibitors, for example
METI acaricides, e.g. Fenazaquin (I212), Fenpyroximate (I213), Pyrimidifen (I214), Pyridaben (I215), Tebufenpyrad (I216), and Tolfenpyrad (I217); or Rotenone (Derris) (I218);

(22) Voltage-dependent sodium channel blockers, e.g. lndoxacarb (I219); or Metaflumizone (I220);

(23) Inhibitors of acetyl CoA carboxylase, for example tetronic and tetramic acid derivatives, e.g. Spirodiclofen (I221), Spiromesifen (I222), and Spirotetramat (I223);

(24) Mitochondrial complex IV electron transport inhibitors, for example phosphines, e.g. Aluminium phosphide (I224), Calcium phosphide (I225), Phosphine (I226), and Zinc phosphide (I227); or Cyanide (I228);

(25) Mitochondrial complex II electron transport inhibitors, for example beta-ketonitrile derivatives, e.g. Cyenopyrafen (I229) and Cyflumetofen (I230);

(26) Ryanodine receptor modulators, for example diamides, e.g. Chlorantraniliprole (I231), Cyantraniliprole (I232), and Flubendiamide (I233);

Further active ingredients with unknown or uncertain mode of action, for example Amidoflumet (I234), Azadirachtin (I235), Benclothiaz (I236), Benzoximate (I237), Bifenazate (I238), Bromopropylate (I239), Chinomethionat (I240), Cryolite (I241), Dicofol (I242), Diflovidazin (I243), Fluensulfone (I244), Flufenerim (I245), Flufiprole (I246), Fluopyram (I247), Fufenozide (I248), lmidaclothiz (I249), Iprodione (I250), Meperfluthrin (I251), Pyridalyl (I252), Pyrifluquinazon (I253), Tetramethylfluthrin (I254), and iodomethane (I255); furthermore products based on *Bacillus firmus* (including but not limited to strain CNCM I-1582, such as, for example, VOTiVO™, BioNem) (I256) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (I257) (known from WO2005/077934), 4-{[(6-bromopyridin-3-yl)methyl](2-fluoroethyl)amino}furan-2 (5H)-one (I258) (known from WO2007/115644), 4-{[(6-fluoropyridin-3-yl)methyl](2,2-difluoroethyl)amino}furan-2(5H)-one (I259) (known from WO2007/115644), 4-{[(2-chloro-1,3-thiazol-5-yl)methyl] (2-fluoroethyl) amino}furan-2(5H)-one (I260) (known from WO2007/115644), 4-{[(6-chlorpyridin-3-yl)methyl](2-fluoroethyl) amino}furan-2(5H)-one (I261) (known from WO2007/115644), Flupyradifurone (I262), 4-{[(6-chlor-5-fluoropyridin-3-yl)methyl](methyl)amino}furan-2(5H)-one (I263) (known from WO2007/115643), 4-{[(5,6-dichloropyridin-3-yl)methyl](2-fluoroethyl)amino}furan-2(5H)-one (I264) (known from WO2007/115646), 4-{[(6-chloro-5-fluoropyridin-3-yl)methyl](cyclopropyl)amino}furan-2

(5H)-one (I265) (known from WO2007/115643), 4-{[(6-chloropyridin-3-yl)methyl](cyclopropyl)amino}furan-2(5H)-one (I266) (known from EP-A-0 539 588), 4-{[(6-chlorpyridin-3-yl)methyl](methyl)amino}furan-2(5H)-one (I267) (known from EP-A-0 539 588), {[1-(6-chloropyridin-3-yl)ethyl](methyl)oxido-λ4-sulfanylidene}cyanamide (I268) (known from WO2007/149134) and its diastereomers {[(1R)-1-(6-chloropyridin-3-yl)ethyl](methyl)oxido-λ4-sulfanylidene}cyanamide (A) (I269), and {[(1S)-1-(6-chloropyridin-3-yl)ethyl](methyl)oxido-λ4-sulfanylidene}cyanamide (B) (I270) (also known from WO2007/149134) as well as diastereomers [(R)-methyl(oxido){(1R)-1-[6-(trifluoromethyl)pyridin-3-yl]ethyl}-λ4-sulfanylidene]cyanamide (A1)) (I271), and [(S)-methyl(oxido){(1S)-1-[6-(trifluoromethyl)pyridin-3-yl]ethyl}-λ4-sulfanylidene]cyanamide (A2) (I272), referred to as group of diastereomers A (known from WO2010/074747, WO2010/074751), [(R)-methyl (oxido){(1S)-1-[6-(trifluoromethyl)pyridin-3-yl]ethyl}-λ4-sulfanylidene]cyanamide (B1) (I273), and [(S)-methyl(oxido){(1R)-1-[6-(trifluoromethyl)pyridin-3-yl]ethyl}-λ4-sulfanylidene]cyanamide (B2) (I274), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (I275) (known from WO2006/089633), 3-(4'-fluoro-2,4-dimethylbiphenyl-3-yl)-4-hydroxy-8-oxa-1-azaspiro[4.5]dec-3-en-2-one (I276) (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (I277) (known from WO2006/043635), Afidopyropen [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (I278) (known from WO2008/066153), 2-cyano-3-(difluoromethoxy)-N,N-dimethylbenzenesulfonamide (I279) (known from WO2006/056433), 2-cyano-3-(difluoromethoxy)-N-methylbenzenesulfonamide (I280) (known from WO2006/100288), 2-cyano-3-(difluoromethoxy)-N-ethyl benzenesulfonamide (I281) (known from WO2005/035486), 4-(difluoromethoxy)-N-ethyl-N-methyl-1,2-benzothiazol-3-amine 1,1-dioxide (I282) (known from WO2007/057407), N-[1-(2,3-dimethylphenyl)-2-(3,5-dimethylphenyl)ethyl]-4,5-dihydro-1,3-thiazol-2-amine (I283) (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (I284) (known from WO2003/106457), 3-(2,5-dimethylphenyl)-4-hydroxy-8-methoxy-1,8-diazaspiro[4.5]dec-3-en-2-one (I285) (known from WO2009/049851), 3-(2,5-dimethylphenyl)-8-methoxy-2-oxo-1,8-diazaspiro[4.5]dec-3-en-4-yl ethyl carbonate (I286) (known from WO2009/049851), 4-(but-2-yn-1-yloxy)-6-(3,5-dimethylpiperidin-1-yl)-5-fluoropyrimidine (I287) (known from WO2004/099160), (2,2,3,3,4,4,5,5-octafluoropentyl)(3,3,3-trifluoropropyl)malononitrile (I288) (known from WO2005/063094), (2,2,3,3,4,4,5,5-octafluoropentyl) (3,3,4,4,4-pentafluorobutyl) malononitrile (I289) (known from WO2005/063094), 8-[2-(cyclopropylmethoxy)-4-(trifluoromethyl) phenoxy]-3-[6-(trifluoromethyl)pyridazin-3-yl]-3-azabicyclo[3.2.1]octane (I290) (known from WO2007/040280), Flometoquin (I291), PF1364 (CAS-Reg.No. 1204776-60-2) (I292) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (I293) (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (I294) (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (I295) (known from WO2005/085216), 4-{[(6-chloropyridin-3-yl)methyl](cyclopropyl)amino}-1,3-oxazol-2(5H)-one (I296), 4-{[(6-chloropyridin-3-yl)methyl](2,2-difluoroethyl)amino}-1,3-oxazol-2(5H)-one (I297), 4-{[(6-chloropyridin-3-yl)methyl](ethyl)amino}-1,3-oxazol-2(5H)-one (I298), 4-{[(6-chloropyridin-3-yl)methyl](methyl)amino}-1,3-oxazol-2(5H)-one (I299) (all known from WO2010/005692), Pyflubumide N-[4-(1,1,1,3,3,3-hexafluoro-2-methoxypropan-2-yl)-3-isobutylphenyl]-N-isobutyryl-1,3,5-trimethyl-1H-pyrazole-4-carboxamide (I300) (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (I301) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (I302) (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (I303) (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (I304) (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (I305) (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (I306) (known from WO2007/101369), 2-{6-[2-(5-fluoropyridin-3-yl)-1,3-thiazol-5-yl]pyridin-2-yl}pyrimidine (I307) (known from WO2010/006713), 2-{6-[2-(pyridin-3-yl)-1,3-thiazol-5-yl]pyridin-2-yl}pyrimidine (I308) (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (I309) (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (I310) (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (I311) (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (I312) (known from WO2010/069502), (1E)-N-[(6-chloropyridin-3-yl)methyl]-N'-cyano-N-(2,2-difluoroethyl)ethanimidamide (I313) (known from WO2008/009360, N-[2-(5-amino-1,3,4-thiadiazol-2-yl)-4-chloro-6-methylphenyl]-3-bromo-1-(3-chloropyridin-2-yl)-1H-pyrazole-5-carboxamide (I314) (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (I315) (known from WO2011/049233)

In one embodiment of the present invention the additional insecticide (II) is selected from the group consisting of Abamectin (I152), Acephate (I27), Acetamiprid (I141), Acrinathrin (I96), Alpha-Cypermethrin (I111), Beta-Cyfluthrin (I106), Bifenthrin (I100), Buprofezin (I202), Clothianidin (I142), Chlorantraniliprole (I231), Chlorfenapyr (I184), Chlorpyrifos (I35), Carbofuran (I8), Cyantraniliprole (I232), Cyenopyrafen (I229), Cyflumentofen (I230), Cyfluthrin (I105), Cypermethrin (I110), Deltamethrin (I116), Diafenthiuron (I178), Dinotefuran (I143), Emamectin-benzoate (I153), Ethiprole (I94), Fenpyroximate (I213), Fipronil (I95), Flometoquin (I291), Flubendiamide (I233), Fluensulfone (I244), Fluopyram (I247), Flupyradifurone (I262), Gamma-Cyhalothrin (I109), Imidacloprid (I144), Indoxacarb (I219), Lambda-Cyhalothrin (I108), Lufenuron (I197), Metaflumizone (I220), Methiocarb (I15), Methoxyfenozide (I206), Milbemectin (I155), Profenofos (I77), Pyflubumide (I300), Pyrifluquinazone (I253), Spinetoram (I150), Spinosad (I151), Spirodiclofen (I221), Spiromesifen (I222), Spirotetramat (I223), Sulfoxaflor (I149), Tebufenpyrad (I216), Tefluthrin (I134), Thiacloprid (I146), Thiamethoxam (I147), Thiodicarb (I21), Triflumuron (I201), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (I309) (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (I310) (known from WO2010/069502) and 1-{2-fluoro-4-methyl-5-[(2,2,2-trifluoroethyl)sulfinyl]phenyl}-3-(trifluoromethyl)-1H-1,2,4-triazol-5-amine (I277).

According to another embodiment the composition according to the invention further comprises at least one fungicide, with the proviso the biological control agent is not identical to the fungicide.

Fungicides

In general, "fungicidal" means the ability of a substance to increase mortality or inhibit the growth rate of fungi.

The term "fungus" or "fungi" includes a wide variety of nucleated sporebearing organisms that are devoid of chlorophyll. Examples of fungi include yeasts, molds, mildews, rusts, and mushrooms.

Preferably, the fungicide is selected so as not to have any fungicidal activity against the biological control agent according to the present invention.

According to one embodiment of the present invention preferred fungicides are selected from the group consisting of (1) Inhibitors of the ergosterol biosynthesis, for example (F1) aldimorph (1704-28-5), (F2) azaconazole (60207-31-0), (F3) bitertanol (55179-31-2), (F4) bromuconazole (116255-48-2), (F5) cyproconazole (113096-99-4), (F6) diclobutrazole (75736-33-3), (F7) difenoconazole (119446-68-3), (F8) diniconazole (83657-24-3), (F9) diniconazole-M (83657-18-5), (F10) dodemorph (1593-77-7), (F11) dodemorph acetate (31717-87-0), (F12) epoxiconazole (106325-08-0), (F13) etaconazole (60207-93-4), (F14) fenarimol (60168-88-9), (F15) fenbuconazole (114369-43-6), (F16) fenhexamid (126833-17-8), (F17) fenpropidin (67306-00-7), (F18) fenpropimorph (67306-03-0), (F19) fluquinconazole (136426-54-5), (F20) flurprimidol (56425-91-3), (F21) flusilazole (85509-19-9), (F22) flutriafol (76674-21-0), (F23) furconazole (112839-33-5), (F24) furconazole-cis (112839-32-4), (F25) hexaconazole (79983-71-4), (F26) imazalil (60534-80-7), (F27) imazalil sulfate (58594-72-2), (F28) imibenconazole (86598-92-7), (F29) ipconazole (125225-28-7), (F30) metconazole (125116-23-6), (F31) myclobutanil (88671-89-0), (F32) naftifine (65472-88-0), (F33) nuarimol (63284-71-9), (F34) oxpoconazole (174212-12-5), (F35) paclobutrazol (76738-62-0), (F36) pefurazoate (101903-30-4), (F37) penconazole (66246-88-6), (F38) piperalin (3478-94-2), (F39) prochloraz (67747-09-5), (F40) propiconazole (60207-90-1), (F41) prothioconazole (178928-70-6), (F42) pyributicarb (88678-67-5), (F43) pyrifenox (88283-41-4), (F44) quinconazole (103970-75-8), (F45) simeconazole (149508-90-7), (F46) spiroxamine (118134-30-8), (F47) tebuconazole (107534-96-3), (F48) terbinafine (91161-71-6), (F49) tetraconazole (112281-77-3), (F50) triadimefon (43121-43-3), (F51) triadimenol (89482-17-7), (F52) tridemorph (81412-43-3), (F53) triflumizole (68694-11-1), (F54) triforine (26644-46-2), (F55) triticonazole (131983-72-7), (F56) uniconazole (83657-22-1), (F57) uniconazole-p (83657-17-4), (F58) viniconazole (77174-66-4), (F59) voriconazole (137234-62-9), (F60) 1-(4-chlorophenyl)-2-(1H-1,2,4-triazol-1-yl)cycloheptanol (129586-32-9), (F61) methyl 1-(2,2-dimethyl-2,3-dihydro-1H-inden-1-yl)-1H-imidazole-5-carboxylate (110323-95-0), (F62) N'-{5-(difluoromethyl)-2-methyl-4-[3-(trimethylsilyl)propoxy]phenyl}-N-ethyl-N-methylimidoformamide, (F63) N-ethyl-N-methyl-N'-{2-methyl-5-(trifluoromethyl)-4-[3-(trimethylsilyl)propoxy]phenyl}imidoformamide, (F64) O-[1-(4-methoxyphenoxy)-3,3-dimethylbutan-2-yl]1H-imidazole-1-carbothioate (111226-71-2);

(2) inhibitors of the respiratory chain at complex I or II, for example (F65) bixafen (581809-46-3), (F66) boscalid (188425-85-6), (F67) carboxin (5234-68-4), (F68) diflumetorim (130339-07-0), (F69) fenfuram (24691-80-3), (F70) fluopyram (658066-35-4), (F71) flutolanil (66332-96-5), (F72) fluxapyroxad (907204-31-3), (F73) furametpyr (123572-88-3), (F74) furmecyclox (60568-05-0), (F75) isopyrazam (mixture of syn-epimeric racemate 1RS,4SR,9RS and anti-epimeric racemate 1RS,4SR,9SR) (881685-58-1), (F76) isopyrazam (anti-epimeric racemate 1RS,4SR,9SR), (F77) isopyrazam (anti-epimeric enantiomer 1R,4S,9S), (F78) isopyrazam (anti-epimeric enantiomer 1S,4R,9R), (F79) isopyrazam (syn epimeric racemate 1RS,4SR,9RS), (F80) isopyrazam (syn-epimeric enantiomer 1R,4S,9R), (F81) isopyrazam (syn-epimeric enantiomer 1S,4R,9S), (F82) mepronil (55814-41-0), (F83) oxycarboxin (5259-88-1), (F84) penflufen (494793-67-8), (F85) penthiopyrad (183675-82-3), (F86) sedaxane (874967-67-6), (F87) thifluzamide (130000-40-7), (F88) 1-methyl-N-[2-(1,1,2,2-tetrafluoroethoxyl)phenyl]-3-(trifluoromethyl)-1H-pyrazole-4-carboxamide, (F89) 3-(difluoromethyl)-1-methyl-N-[2-(1,1,2,2-tetrafluoroethoxyl)phenyl]-1H-pyrazole-4-carboxamide, (F90) 3-(difluoromethyl)-N-[4-fluoro-2-(1,1,2,3,3,3-hexafluoropropoxyl)phenyl]-1-methyl-1H-pyrazole-4-carboxamide, (F91) N-[1-(2,4-dichlorophenyl)-1-methoxypropan-2-yl]-3-(difluoromethyl)-1-methyl-1H-pyrazole-4-carboxamide (1092400-95-7), (F92) 5,8-difluoro-N-[2-(2-fluoro-4-{[4-(trifluoromethyl)pyridin-2-yl]oxy}phenyl)ethyl]quinazolin-4-amine (1210070-84-0), (F93) benzovindiflupyr, (F94) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (F95) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (F96) 3-(Difluormethyl)-1-methyl-N-(1,1,3-trimethyl-2,3-dihydro-1H-inden-4-yl)-1H-pyrazol-4-carboxamid, (F97) 1,3,5-Trimethyl-N-(1,1,3-trimethyl-2,3-dihydro-1H-inden-4-yl)-1H-pyrazol-4-carboxamid, (F98) 1-Methyl-3-(trifluormethyl)-N-(1,3,3-trimethyl-2,3-dihydro-1H-inden-4-yl)-1H-pyrazol-4-carboxamid, (F99) 1-Methyl-3-(trifluormethyl)-N-[(1S)-1,3,3-trimethyl-2,3-dihydro-1H-inden-4-yl]-1H-pyrazol-4-carboxamid, (F100) 1-Methyl-3-(trifluormethyl)-N-[(1R)-1,3,3-trimethyl-2,3-dihydro-1H-inden-4-yl]-1H-pyrazol-4-carboxamid, (F101) 3-(Difluormethyl)-1-methyl-N-[(3S)-1,1,3-trimethyl-2,3-dihydro-1H-inden-4-yl]-1H-pyrazol-4-carboxamid, (F102) 3-(Difluormethyl)-1-methyl-N-[(3R)-1,1,3-trimethyl-2,3-dihydro-1H-inden-4-yl]-1H-pyrazol-4- carboxamid, (F103) 1,3,5-Trimethyl-N-[(3R)-1,1,3-trimethyl-2,3-dihydro-1H-inden-4-yl]-1H-pyrazol-4-carboxamid, (F104) 1,3,5-Trimethyl-N-[(3S)-1,1,3-trimethyl-2,3-dihydro-1H-inden-4-yl]-1H-pyrazol-4-carboxamid;

(3) inhibitors of the respiratory chain at complex III, for example (F105) ametoctradin (865318-97-4), (F106) amisulbrom (348635-87-0), (F107) azoxystrobin (131860-33-8), (F108) cyazofamid (120116-88-3), (F109) coumethoxystrobin (850881-30-0), (F110) coumoxystrobin (850881-70-8), (F111) dimoxystrobin (141600-52-4), (F112) enestroburin (238410-11-2), (F113) famoxadone (131807-57-3), (F114) fenamidone (161326-34-7), (F115) fenoxystrobin (918162-02-4), (F116) fluoxastrobin (361377-29-9), (F117) kresoxim-methyl (143390-89-0), (F118) metominostrobin (133408-50-1), (F119) orysastrobin (189892-69-1), (F120) picoxystrobin (117428-22-5), (F121) pyraclostrobin (175013-18-0), (F122) pyrametostrobin (915410-70-7), (F123) pyraoxystrobin (862588-11-2), (F124) pyribencarb (799247-52-2), (F125) triclopyricarb (902760-40-1), (F126) trifloxystrobin (141517-21-7), (F127) (2E)-2-(2-{[6-(3-chloro-2-methylphenoxy)-5-fluoropyrimidin-4-yl]oxy}phenyl)-2-(methoxyimino)-N-methylethanamide, (F128) (2E)-2-(methoxyimino)-N-methyl-2-(2-{[({(1E)-1-[3-(trifluoromethyl)phenyl]ethylidene}amino)oxy]methyl}phenyl)ethanamide, (F129) (2E)-2-(methoxyimino)-N-methyl-2-{2-[(E)-({1-[3-(trifluoromethyl)phenyl]ethoxy}imino)methyl]phenyl}ethanamide (158169-73-4), (F130) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (F131) (2E)-2-{2-[({[(2E,3E)-4-(2,6-dichlorophenyl)but-3-en-2-ylidene]amino}oxy)methyl]phenyl}-2-(methoxyimino)-N-methylethanamide, (F132) 2-chloro-N-(1,1,3-trimethyl-2,3-dihydro-1H-inden-4-yl)pyridine-3-carboxamide (119899-14-8), (F133) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (F134) methyl (2E)-2-{2-[({cyclopropyl[(4-methoxyphenyl)imino]methyl}sulfanyl)methyl]phenyl}-3-methoxyprop-2-enoate (149601-03-6), (F135) N-(3-ethyl-3,5,5-trimethylcyclohexyl)-3-(formylamino)-2-hydroxybenzamide (226551-21-9), (F136) 2-{2-[(2,5-dimethylphenoxy)methyl]phenyl}-2-methoxy-N-methylacetamide (173662-97-0), (F137) (2R)-2-{2-[(2,5-dimethylphenoxy)methyl]phenyl}-2-methoxy-N-methylacetamide (394657-24-0);

(4) Inhibitors of the mitosis and cell division, for example (F138) benomyl (17804-35-2), (F139) carbendazim (10605-21-7), (F140) chlorfenazole (3574-96-7), (F141) diethofencarb (87130-20-9), (F142) ethaboxam (162650-77-3), (F143) fluopicolide (239110-15-7), (F144) fuberidazole (3878-19-1), (F145) pencycuron (66063-05-6), (F146) thiabendazole (148-79-8), (F147) thiophanate-methyl (23564-05-8), (F148) thiophanate (23564-06-9), (F149) zoxamide (156052-68-5), (F150) 5-chloro-7-(4-methylpiperidin-1-yl)-6-(2,4,6-trifluorophenyl) [1,2,4]triazolo[1,5-a]pyrimidine (214706-53-3), (F151) 3-chloro-5-(6-chloropyridin-3-yl)-6-methyl-4-(2,4,6-trifluorophenyl)pyridazine (1002756-87-7);

(5) Compounds capable to have a multisite action, like for example (F152) bordeaux mixture (8011-63-0), (F153) captafol (2425-06-1), (F154) captan (133-06-2), (F155) chlorothalonil (1897-45-6), (F156) copper hydroxide (20427-59-2), (F157) copper naphthenate (1338-02-9), (F158) copper oxide (1317-39-1), (F159) copper oxychloride (1332-40-7), (F160) copper(2+) sulfate (7758-98-7), (F161) dichlofluanid (1085-98-9), (F162) dithianon (3347-22-6), (F163) dodine (2439-10-3), (F164) dodine free base, (F165) ferbam (14484-64-1), (F166) fluorofolpet (719-96-0), (F167) folpet (133-07-3), (F168) guazatine (108173-90-6), (F169) guazatine acetate, (F170) iminoctadine (13516-27-3), (F171) iminoctadine albesilate (169202-06-6), (F172) iminoctadine triacetate (57520-17-9), (F173) mancopper (53988-93-5), (F174) mancozeb (8018-01-7), (F175) maneb (12427-38-2), (F176) metiram (9006-42-2), (F177) metiram zinc (9006-42-2), (F178) oxine-copper (10380-28-6), (F179) propamidine (104-32-5), (F180) propineb (12071-83-9), (F181) sulphur and sulphur preparations including calcium polysulphide (7704-34-9), (F182) thiram (137-26-8), (F183) tolylfluanid (731-27-1), (F184) zineb (12122-67-7), (F185) ziram (137-30-4);

(6) Compounds capable to induce a host defence, like for example (F186) acibenzolar-S-methyl (135158-54-2), (F187) isotianil (224049-04-1), (F188) probenazole (27605-76-1), (F189) tiadinil (223580-51-6);

(7) Inhibitors of the amino acid and/or protein biosynthesis, for example (F190) andoprim (23951-85-1), (F191) blasticidin-S(2079-00-7), (F192) cyprodinil (121552-61-2), (F193) kasugamycin (6980-18-3), (F194) kasugamycin hydrochloride hydrate (19408-46-9), (F195) mepanipyrim (110235-47-7), (F196) pyrimethanil (53112-28-0), (F197) 3-(5-fluoro-3,3,4,4-tetramethyl-3,4-dihydroisoquinolin-1-yl)quinoline (861647-32-7);

(8) Inhibitors of the ATP production, for example (F198) fentin acetate (900-95-8), (F199) fentin chloride (639-58-7), (F200) fentin hydroxide (76-87-9), (F201) silthiofam (175217-20-6);

(9) Inhibitors of the cell wall synthesis, for example (F202) benthiavalicarb (177406-68-7), (F203) dimethomorph (110488-70-5), (F204) flumorph (211867-47-9), (F205) iprovalicarb (140923-17-7), (F206) mandipropamid (374726-62-2), (F207) polyoxins (11113-80-7), (F208) polyoxorim (22976-86-9), (F209) validamycin A (37248-47-8), (F210) valifenalate (283159-94-4; 283159-90-0);

(10) Inhibitors of the lipid and membrane synthesis, for example (F211) biphenyl (92-52-4), (F212) chloroneb (2675-77-6), (F213) dicloran (99-30-9), (F214) edifenphos (17109-49-8), (F215) etridiazole (2593-15-9), (F216) iodocarb (55406-53-6), (F217) iprobenfos (26087-47-8), (F218) isoprothiolane (50512-35-1), (F219) propamocarb (25606-41-1), (F220) propamocarb hydrochloride (25606-41-1), (F221) prothiocarb (19622-08-3), (F222) pyrazophos (13457-18-6), (F223) quintozene (82-68-8), (F224) tecnazene (117-18-0), (F225) tolclofos-methyl (57018-04-9);

(11) Inhibitors of the melanine biosynthesis, for example (F226) carpropamid (104030-54-8), (F227) diclocymet (139920-32-4), (F228) fenoxanil (115852-48-7), (F229) phthalide (27355-22-2), (F230) pyroquilon (57369-32-1), (F231) tricyclazole (41814-78-2), (F232) 2,2,2-trifluoroethyl {3-methyl-1-[(4-methylbenzoyl)amino]butan-2-yl}carbamate (851524-22-6);

(12) Inhibitors of the nucleic acid synthesis, for example (F233) benalaxyl (71626-11-4), (F234) benalaxyl-M (kiralaxyl) (98243-83-5), (F235) bupirimate (41483-43-6), (F236) clozylacon (67932-85-8), (F237) dimethirimol (5221-53-4), (F238) ethirimol (23947-60-6), (F239) furalaxyl (57646-30-7), (F240) hymexazol (10004-44-1), (F241) metalaxyl (57837-19-1), (F242) metalaxyl-M (mefenoxam) (70630-17-0), (F243) ofurace (58810-48-3), (F244) oxadixyl (77732-09-3), (F245) oxolinic acid (14698-29-4);

(13) Inhibitors of the signal transduction, for example (F246) chlozolinate (84332-86-5), (F247) fenpiclonil (74738-17-3), (F248) fludioxonil (131341-86-1), (F249)

iprodione (36734-19-7), (F250) procymidone (32809-16-8), (F251) quinoxyfen (124495-18-7), (F252) vinclozolin (50471-44-8);

(14) Compounds capable to act as an uncoupler, like for example (F253) binapacryl (485-31-4), (F254) dinocap (131-72-6), (F255) ferimzone (89269-64-7), (F256) fluazinam (79622-59-6), (F257) meptyldinocap (131-72-6);

(15) Further compounds, like for example (F258) benthiazole (21564-17-0), (F259) bethoxazin (163269-30-5), (F260) capsimycin (70694-08-5), (F261) carvone (99-49-0), (F262) chinomethionat (2439-01-2), (F263) pyriofenone (chlazafenone) (688046-61-9), (F264) cufraneb (11096-18-7), (F265) cyflufenamid (180409-60-3), (F266) cymoxanil (57966-95-7), (F267) cyprosulfamide (221667-31-8), (F268) dazomet (533-74-4), (F269) debacarb (62732-91-6), (F270) dichlorophen (97-23-4), (F271) diclomezine (62865-36-5), (F272) difenzoquat (49866-87-7), (F273) difenzoquat methylsulphate (43222-48-6), (F724) diphenylamine (122-39-4), (F275) ecomate, (F276) fenpyrazamine (473798-59-3), (F277) flumetover (154025-04-4), (F278) fluoroimide (41205-21-4), (F279) flusulfamide (106917-52-6), (F280) flutianil (304900-25-2), (F281) fosetyl-aluminium (39148-24-8), (F282) fosetyl-calcium, (F283) fosetyl-sodium (39148-16-8), (F284) hexachlorobenzene (118-74-1), (F285) irumamycin (81604-73-1), (F286) methasulfocarb (66952-49-6), (F287) methyl isothiocyanate (556-61-6), (F288) metrafenone (220899-03-6), (F289) mildiomycin (67527-71-3), (F290) natamycin (7681-93-8), (F291) nickel dimethyldithiocarbamate (15521-65-0), (F292) nitrothal-isopropyl (10552-74-6), (F293) octhilinone (26530-20-1), (F294) oxamocarb (917242-12-7), (F295) oxyfenthiin (34407-87-9), (F296) pentachlorophenol and salts (87-86-5), (F297) phenothrin, (F298) phosphorous acid and its salts (13598-36-2), (F299) propamocarb-fosetylate, (F300) propanosine-sodium (88498-02-6), (F301) proquinazid (189278-12-4), (F302) pyrimorph (868390-90-3), (F303) (2E)-3-(4-tert-butylphenyl)-3-(2-chloropyridin-4-yl)-1-(morpholin-4-yl)prop-2-en-1-one (1231776-28-5), (F304) (2Z)-3-(4-tert-butylphenyl)-3-(2-chloropyridin-4-yl)-1-(morpholin-4-yl)prop-2-en-1-one (1231776-29-6), (F305) pyrrolnitrine (1018-71-9), (F306) tebufloquin (376645-78-2), (F307) tecloftalam (76280-91-6), (F308) tolnifanide (304911-98-6), (F309) triazoxide (72459-58-6), (F310) trichlamid (70193-21-4), (F311) zarilamid (84527-51-5), (F312) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methyl propanoate (517875-34-2), (F313) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (F314) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (F315) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (F316) 1-(4-methoxyphenoxy)-3,3-dimethylbutan-2-yl 1H-imidazole-1-carboxylate (111227-17-9), (F317) 2,3,5,6-tetrachloro-4-(methylsulfonyl)pyridine (13108-52-6), (F318) 2,3-dibutyl-6-chlorothieno[2,3-d]pyrimidin-4(3H)-one (221451-58-7), (F319) 2,6-dimethyl-1H,5H-[1,4]dithiino[2,3-c:5,6-c]dipyrrole-1,3,5,7(2H,6H)-tetrone, (F320) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (F321) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (F322) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (F323) 2-butoxy-6-iodo-3-propyl-4H-chromen-4-one, (F324) 2-chloro-5-[2-chloro-1-(2,6-difluoro-4-methoxyphenyl)-4-methyl-1H-imidazol-5-yl]pyridine, (F325) 2-phenylphenol and salts (90-43-7), (F326) 3-(4,4,5-trifluoro-3,3-dimethyl-3,4-dihydroisoquinolin-1-yl)quinoline (861647-85-0), (F327) 3,4,5-trichloropyridine-2,6-dicarbonitrile (17824-85-0), (F328) 3-[5-(4-chlorophenyl)-2,3-dimethyl-1,2-oxazolidin-3-yl]pyridine, (F329) 3-chloro-5-(4-chlorophenyl)-4-(2,6-difluorophenyl)-6-methylpyridazine, (F330) 4-(4-chlorophenyl)-5-(2,6-difluorophenyl)-3,6-dimethylpyridazine, (F331) 5-amino-1,3,4-thiadiazole-2-thiol, (F332) 5-chloro-N'-phenyl-N'-(prop-2-yn-1-yl)thiophene-2-sulfonohydrazide (134-31-6), (F333) 5-fluoro-2-[(4-fluorobenzyl)oxy]pyrimidin-4-amine (1174376-11-4), (F334) 5-fluoro-2-[(4-methylbenzyl)oxy]pyrimidin-4-amine (1174376-25-0), (F335) 5-methyl-6-octyl[1,2,4]triazolo[1,5-a]pyrimidin-7-amine, (F336) ethyl (2Z)-3-amino-2-cyano-3-phenylprop-2-enoate, (F337) N'-(4-{[3-(4-chlorobenzyl)-1,2,4-thiadiazol-5-yl]oxy}-2,5-dimethylphenyl)-N-ethyl-N-methylimidoformamide, (F338) N-(4-chlorobenzyl)-3-[3-methoxy-4-(prop-2-yn-1-yloxy)phenyl]propanamide, (F339) N-[(4-chlorophenyl)(cyano) methyl]-3-[3-methoxy-4-(prop-2-yn-1-yloxy)phenyl]propanamide, (F340) N-[(5-bromo-3-chloropyridin-2-yl)methyl]-2,4-dichloropyridine-3-carboxamide, (F341) N-[1-(5-bromo-3-chloropyridin-2-yl)ethyl]-2,4-dichloropyridine-3-carboxamide, (F342) N-[1-(5-bromo-3-chloropyridin-2-yl)ethyl]-2-fluoro-4-iodopyridine-3-carboxamide, (F343) N-{(E)-[(cyclopropylmethoxy)imino][6-(difluoromethoxy)-2,3-difluorophenyl]methyl}-2-phenylacetamide (221201-92-9), (F344) N-{(Z)-[(cyclopropylmethoxy)imino][6-(difluoromethoxy)-2,3-difluorophenyl]methyl}-2-phenylacetamide (221201-92-9), (F345) N'-{4-[(3-tert-butyl-4-cyano-1,2-thiazol-5-yl)oxy]-2-chloro-5-methylphenyl}-N-ethyl-N-methylimidoformamide, (F346) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (F347) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (F348) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (F349) pentyl{6-[({[(1-methyl-1H-tetrazol-5-yl)(phenyl)methylidene]amino}oxy)methyl]pyridin-2-yl}carbamate, (F350) phenazine-1-carboxylic acid, (F351) quinolin-8-ol (134-31-6), (F352) quinolin-8-ol sulfate (2:1) (134-31-6), (F353) tert-butyl {6-[({[(1-methyl-1H-tetrazol-5-yl) (phenyl)methylene]amino}oxy)methyl]pyridin-2-yl}carbamate;

(16) Further compounds, like for example (F354) 1-methyl-3-(trifluoromethyl)-N-[2'-(trifluoromethyl)biphenyl-2-yl]-1H-pyrazole-4-carboxamide, (F355) N-(4'-chlorobiphenyl-2-yl)-3-(difluoromethyl)-1-methyl-1H-pyrazole-4-carboxamide, (F356) N-(2',4'-dichlorobiphenyl-2-yl)-3-(difluoromethyl)-1-methyl-1H-pyrazole-4-carboxamide, (F357) 3-(difluoromethyl)-1-methyl-N-[4'-(trifluoromethyl)biphenyl-2-yl]-1H-pyrazole-4-carboxamide, (F358) N-(2',5'-difluorobiphenyl-2-yl)-1-methyl-3-(trifluoromethyl)-1H-pyrazole-4-carboxamide, (F359) 3-(difluoromethyl)-1-methyl-N-[4'-(prop-1-yn-1-yl)biphenyl-2-yl]-1H-pyrazole-4-carboxamide, (F360) 5-fluoro-1,3-dimethyl-N-[4'-(prop- 1-yn-1-yl)biphenyl-2-yl]-1H-pyrazole-4-carboxamide, (F361) 2-chloro-N-[4'-(prop-1-yn-1-yl)biphenyl-2-yl]pyridine-3-carboxamide, (F362) 3-(difluoromethyl)-N-[4'-(3,3-dimethylbut-1-yn-1-yl)biphenyl-2-yl]-1-methyl-1H-pyrazole-4-carboxamide, (F363) N-[4'-(3,3-dimethylbut-1-yn-1-yl)biphenyl-2-yl]-5-fluoro-1,3-dimethyl-1H-pyrazole-4-carboxamide, (F364) 3-(difluoromethyl)-N-(4'-ethynylbiphenyl-2-yl)-1-methyl-1H-pyrazole-4-carboxamide, (F365) N-(4'-ethynylbiphenyl-2-yl)-5-fluoro-1,3-dimethyl-1H-pyrazole-4-carboxamide, (F366) 2-chloro-N-(4'-ethynylbiphenyl-2-yl)pyridine-3-carboxamide, (F367) 2-chloro-N-[4'-(3,3-dimethylbut-1-yn-1-yl)biphenyl-2-yl]pyridine-3-carboxamide, (F368) 4-(difluoromethyl)-2-methyl-N-[4'-(trifluoromethyl)biphenyl-2-yl]-1,3-thiazole-5-carboxamide, (F369) 5-fluoro-N-[4'-(3-hydroxy-3-methylbut-1-yn-1-yl)biphenyl-2-yl]-1,3-dimethyl-1H-pyrazole-4-carboxamide, (F370) 2-chloro-N-[4'-(3-hydroxy-3-methylbut-1-yn-1-yl)biphenyl-2-yl]pyridine-3-carboxamide, (F371) 3-(difluoromethyl)-N-[4'-(3-methoxy-3-methylbut-1-yn-1-yl)biphenyl-2-yl]-1-methyl-1H-pyrazole-4-carboxamide, (F372) 5-fluoro-N-[4'-(3-methoxy-3-methylbut-1-yn-1-yl)biphenyl-2-yl]-1,3-dimethyl-1H-pyrazole-4-carboxamide, (F373) 2-chloro-N-[4'-(3-methoxy-3-methylbut-1-yn-1-yl)biphenyl-2-yl]pyridine-3-carboxamide, (F374) (5-bromo-2-methoxy-4-methylpyridin-3-yl)(2,3,4-trimethoxy-6-methylphenyl)methanone, (F375) N-[2-(4-{[3-(4-chlorophenyl)prop-2-yn-1-yl]oxy}-3-methoxyphenyl)ethyl]-N2-(methylsulfonyl)valinamide (220706-93-4), (F376) 4-oxo-4-[(2-phenylethyl)amino]butanoic acid, (F377) but-3-yn-1-yl {6-[({[(Z)-(1-methyl-1H-tetrazol-5-yl)(phenyl)methylene]amino}oxy)methyl]pyridin-2-yl}carbamate, (F378) 4-Amino-5-fluoropyrimidin-2-ol (mesomere Form: 6-Amino-5-fluoropyrimidin-2(1H)-on), (F379) propyl 3,4,5-trihydroxybenzoate and (F380) Oryzastrobin.

All named fungicides of the classes (1) to (16) (i. e. F1 to F380) can, if their functional groups enable this, optionally form salts with suitable bases or acids.

In a preferred embodiment of the present invention the at least fungicide is a synthetic fungicide.

According to a preferred embodiment of the present invention the fungicide is selected from the group consisting of (1) Inhibitors of the ergosterol biosynthesis, for example (F3) bitertanol, (F4) bromuconazole (116255-48-2), (F5) cyproconazole (113096-99-4), (F7) difenoconazole (119446-68-3), (F12) epoxiconazole (106325-08-0), (F16) fenhexamid (126833-17-8), (F17) fenpropidin (67306-00-7), (F18) fenpropimorph (67306-03-0), (F19) fluquinconazole (136426-54-5), (F22) flutriafol, (F26) imazalil, (F29) ipconazole (125225-28-7), (F30) metconazole (125116-23-6), (F31) myclobutanil (88671-89-0), (F37) penconazole (66246-88-6), (F39) prochloraz (67747-09-5), (F40) propiconazole (60207-90-1), (F41) prothioconazole (178928-70-6), (F44) quinconazole (103970-75-8), (F46) spiroxamine (118134-30-8), (F47) tebuconazole (107534-96-3), (F51) triadimenol (89482-17-7), (F55) triticonazole (131983-72-7);

(2) inhibitors of the respiratory chain at complex I or II, for example (F65) bixafen (581809-46-3), (F66) boscalid (188425-85-6), (F67) carboxin (5234-68-4), (F70) fluopyram (658066-35-4), (F71) flutolanil (66332-96-5), (F72) fluxapyroxad (907204-31-3), (F73) furametpyr (123572-88-3), (F75) isopyrazam (mixture of syn-epimeric racemate 1RS,4SR,9SR and anti-epimeric racemate 1RS,4SR,9SR) (881685-58-1), (F76) isopyrazam (anti-epimeric racemate 1RS,4SR,9SR), (F77) isopyrazam (anti-epimeric enantiomer 1R,4S,9S), (F78) isopyrazam (anti-epimeric enantiomer 1S,4R,9R), (F79) isopyrazam (syn epimeric racemate 1 RS,4SR,9RS), (F80) isopyrazam (syn-epimeric enantiomer 1R,4S,9R), (F81) isopyrazam (syn-epimeric enantiomer 1S,4R,9S), (F84) penflufen (494793-67-8), (F85) penthiopyrad (183675-82-3), (F86) sedaxane (874967-67-6), (F87) thifluzamide (130000-40-7), (F91) N-[1-(2,4-dichlorophenyl)-1-methoxypropan-2-yl]-3-(difluoromethyl)-1-methyl-1H-pyrazole-4-carboxamide (1092400-95-7), (F98) 1-Methyl-3-(trifluormethyl)-N-(1,3,3-trimethyl-2,3-dihydro-1H-inden-4-yl)-1H-pyrazol-4-carboxamid, (F99) 1-Methyl-3-(trifluormethyl)-N-[(1S)-1,3,3-trimethyl-2,3-dihydro-1H-inden-4-yl]-1H-pyrazol-4-carboxamid, (F100) 1-Methyl-3-(trifluormethyl)-N-[(1R)-1,3,3-trimethyl-2,3-dihydro-1H-inden-4-yl]-1H-pyrazol-4-carboxamid, (F101) 3-(Difluormethyl)-1-methyl-N-[(3S)-1,1,3-trimethyl-2,3-dihydro-1H-inden-4-yl]-1H-pyrazol-4-carboxamid, (F102) 3-(Difluormethyl)-1-methyl-N-[(3R)-1,1,3-trimethyl-2,3-dihydro-1H-inden-4-yl]-1H-pyrazol-4-carboxamid;

(3) inhibitors of the respiratory chain at complex III, for example (F105) ametoctradin (865318-97-4), (F106) amisulbrom (348635-87-0), (F107) azoxystrobin (131860-33-8), (F108) cyazofamid (120116-88-3), (F111) dimoxystrobin (141600-52-4), (F112) enestroburin (238410-11-2), (F113) famoxadone (131807-57-3), (F114) fenamidone (161326-34-7), (F116) fluoxastrobin (361377-29-9), (F117) kresoxim-methyl (143390-89-0), (F118) metominostrobin (133408-50-1), (F119) orysastrobin (189892-69-1), (F120) picoxystrobin (117428-22-5), (F121) pyraclostrobin (175013-18-0), (F124) pyribencarb (799247-52-2), (F126) trifloxystrobin (141517-21-7);

(4) Inhibitors of the mitosis and cell division, for example (F139) carbendazim (10605-21-7), (F140) chlorfenazole (3574-96-7), (F141) diethofencarb (87130-20-9), (F142) ethaboxam (162650-77-3), (F143) fluopicolide, (F144) fuberidazole (3878-19-1), (F145) pencycuron (66063-05-6), (F147) thiophanate-methyl (23564-05-8), (F149) zoxamide (156052-68-5);

(5) Compounds capable to have a multisite action, like for example (F154) captan (133-06-2), (F155) chlorothalonil (1897-45-6), (F156) copper hydroxide (20427-59-2), (F159) copper oxychloride (1332-40-7), (F162) dithianon (3347-22-6), (F163) dodine (2439-10-3), (F167) fol pet (133-07-3), (F168) guazatine (108173-90-6), (F172) iminoctadine triacetate (57520-17-9), (F174) mancozeb (8018-01-7), (F180) propineb (12071-83-9), (F181) sulphur and sulphur preparations including calcium polysulphide (7704-34-9), (F182) thiram (137-26-8);

(6) Compounds capable to induce a host defence, like for example (F186) acibenzolar-S-methyl (135158-54-2), (F187) isotianil (224049-04-1), (F189) tiadinil (223580-51-6);

(7) Inhibitors of the amino acid and/or protein biosynthesis, for example (F192) cyprodinil (121552-61-2), (F196) pyrimethanil (53112-28-0);

(8) Inhibitors of the cell wall synthesis, for example (F202) benthiavalicarb (177406-68-7), (F203) dimethomorph (110488-70-5), (F205) iprovalicarb (140923-17-7), (F206) mandiproa mid (374726-62-2), (F210) valifenalate (283159-94-4; 283159-90-0);

(9) Inhibitors of the lipid and membrane synthesis, for example (F216) iodocarb (55406-53-6), (F217) iprobenfos (26087-47-8), (F220) propamocarb hydrochloride (25606-41-1), (F225) tolclofos-methyl;

(10) Inhibitors of the melanine biosynthesis, for example (F226) carpropamid

(11) Inhibitors of the nucleic acid synthesis, for example (F233) benalaxyl (71626-11-4), (F234) benalaxyl-M (kiralaxyl) (98243-83-5), (F239) furalaxyl (57646-30-7), (F240) hymexazol (10004-44-1), (F241) metalaxyl (57837-19-1), (F242) metalaxyl-M (mefenoxam) (70630-17-0), (F244) oxadixyl (77732-09-3);

(12) Inhibitors of the signal transduction, for example (F247) fenpiclonil (74738-17-3), (F248) fludioxonil (131341-86-1), (F249) iprodione (36734-19-7), (F251) quinoxyfen (124495-18-7), (F252) vinclozolin (50471-44-8);

(13) Compounds capable to act as an uncoupler, like for example (F256) fluazinam (79622-59-6);

(14) Further compounds, like for example (F266) cymoxanil (57966-95-7), (F280) flutianil (304900-25-2), (F281) fosetyl-aluminium (39148-24-8), (F286) methasulfocarb (66952-49-6), (F287) methyl isothiocyanate (556-61-6), (F288) metrafenone (220899-03-6), (F298) phosphorous acid and its salts (13598-36-2), (F301) proquinazid (189278-12-4), (F309) triazoxide (72459-58-6) and (F319) 2,6-dimethyl-1H,5H-[1,4]dithiino[2,3-c:5,6-c']dipyrrole-1,3,5,7 (2H,6H)-tetrone.

Further Additives

One aspect of the present invention is to provide a composition as described above additionally comprising at least one auxiliary selected from the group consisting of extenders, solvents, spontaneity promoters, carriers, emulsifiers, dispersants, frost protectants, thickeners and adjuvants. Those compositions are referred to as formulations.

Accordingly, in one aspect of the present invention such formulations, and application forms prepared from them, are provided as crop protection agents and/or pesticidal agents, such as drench, drip and spray liquors, comprising the composition of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation. The content of the active compound is defined as the sum of the at least one biological control agent and the at least one insecticide (I).

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

Kit of Parts

Furthermore, in one aspect of the present invention a kit of parts is provided comprising the composition according to the present invention in a spatially separated arrangement.

In a further embodiment of the present invention the above-mentioned kit of parts further comprises at least one additional insecticide (II) and/or at least one fungicide, with the proviso that insecticide (II) is not identical to insecticide (I) and the biological control agent is not identical to the fungicide. The fungicide can be present either in the biological control agent component of the kit of parts or in the insecticide component of the kit of parts being spatially separated or in both of these components. Preferably, the fungicide is present in the insecticide component. Moreover, the kit of parts according to the present invention can additionally comprise at least one auxiliary selected from the group consisting of extenders, solvents, spontaneity promoters, carriers, emulsifiers, dispersants, frost protectants, thickeners and adjuvants as mentioned below. This at least one auxiliary can be present either in the biological control agent component of the kit of parts or in the insecticide component of the kit of parts being spatially separated or in both of these components.

In another aspect of the present invention the composition as described above is used for reducing overall damage of plants and plant parts as well as losses in harvested fruits or vegetables caused by insects, nematodes and/or phytopathogens.

Furthermore, in another aspect of the present invention the composition as described above increases the overall plant health.

The term "plant health" generally comprises various sorts of improvements of plants that are not connected to the control of pests. For example, advantageous properties that may be mentioned are improved crop characteristics including: emergence, crop yields, protein content, oil content, starch content, more developed root system, improved root growth, improved root size maintenance, improved root effectiveness, improved stress tolerance (e.g. against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

With regard to the use according to the present invention, improved plant health preferably refers to improved plant characteristics including: crop yield, more developed root system (improved root growth), improved root size maintenance, improved root effectiveness, tillering increase, increase in plant height, bigger leaf blade, less dead basal leaves, stronger tillers, greener leaf color, photosynthetic activity, more productive tillers, enhanced plant vigor, and increased plant stand.

With regard to the present invention, improved plant health preferably especially refers to improved plant properties selected from crop yield, more developed root system, improved root growth, improved root size maintenance, improved root effectiveness, tillering increase, and increase in plant height.

The effect of a composition according to the present invention on plant health as defined herein can be determined by comparing plants which are grown under the same environmental conditions, whereby a part of said plants is treated with a composition according to the present invention and another part of said plants is not treated with a composition according to the present invention. Instead, said other part is not treated at all or treated with a placebo (i.e., an application without a composition according to the invention such as an application without all active ingredients (i.e. without a biological control agent as described herein and without an insecticide as described herein), or an application without a biological control agent as described herein, or an application without an insecticide as described herein.

The composition according to the present invention may be applied in any desired manner, such as in the form of a seed coating, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow (plant's locus of growth).

Reducing the overall damage of plants and plant parts often results in healthier plants and/or in an increase in plant vigor and yield.

Preferably, the composition according to the present invention is used for treating conventional or transgenic plants or seed thereof.

In another aspect of the present invention a method for reducing overall damage of plants and plant parts as well as losses in harvested fruits or vegetables caused by insects, nematodes and/or phytopathogens is provided comprising the step of simultaneously or sequentially applying the composition of the present invention and optionally at least one additional insecticide (II) and/or at least one fungicide on the plant, plant parts, harvested fruits, vegetables and/or plant's locus of growth in a synergistically effective amount.

The method of the present invention includes the following application methods, namely both of the at least one biological control agent and the at least one insecticide (I) mentioned before may be formulated into a single, stable composition with an agriculturally acceptable shelf life (so called "solo-formulation"), or being combined before or at the time of use (so called "combined-formulations").

If not mentioned otherwise, the expression "combination" stands for the various combinations of the at least one biological control agent and the at least one insecticide (I), and optionally at least one additional insecticide (II) and/or at least one fungicide, in a solo-formulation, in a single "ready-mix" form, in a combined spray mixture composed from solo-formulations, such as a "tank-mix", and especially in a combined use of the single active ingredients when applied in a sequential manner, i.e. one after the other within a reasonably short period, such as a few hours or days, e.g. 2 hours to 7 days. The order of applying the composition according to the present invention is not essential for working the present invention. Accordingly, the term "combination" also encompasses the presence of the at least one biological control agent and the at least one insecticide (I), and optionally the at least one additional insecticide (II) and/or at least one fungicide on or in a plant to be treated or its surrounding, habitat or storage space, e.g. after simultaneously or consecutively applying the at least one biological control agent and the at least one insecticide (I), and optionally the at least one additional insecticide (II) and/or at least one fungicide to a plant its surrounding, habitat or storage space.

If the at least one biological control agent and the at least one insecticide (I), and optionally the at least one additional insecticide (II) and/or at least one fungicide are employed or used in a sequential manner, it is preferred to treat the plants or plant parts (which includes seeds and plants emerging from the seed), harvested fruits and vegetables according to the following method: Firstly applying the at least one insecticide (I) and optionally the at least one additional insecticide (II) and/or at least one fungicide on the plant or plant parts, and secondly applying the biological control agent to the same plant or plant parts. The time periods between the first and the second application within a (crop) growing cycle may vary and depend on the effect to be achieved. For example, the first application is done to prevent an infestation of the plant or plant parts with insects, nematodes and/or phytopathogens (this is particularly the case when treating seeds) or to combat the infestation with insects, nematodes and/or phytopathogens (this is particularly the case when treating plants and plant parts) and the second application is done to prevent or control the infestation with insects, nematodes and/or phytopathogens. Control in this context means that the biological control agent is not able to fully exterminate the pests or phytopathogenic fungi but is able to keep the infestation on an acceptable level.

By following the before mentioned steps, a very low level of residues of the at least one insecticide (I), and optionally at least one additional insecticide (II) and/or at least one fungicide on the treated plant, plant parts, and the harvested fruits and vegetables can be achieved.

If not mentioned otherwise the treatment of plants or plant parts (which includes seeds and plants emerging from the seed), harvested fruits and vegetables with the composition according to the invention is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the at least one biological control agent, the at least one insecticide (I), and optionally the at least one additional insecticide (II) and/or at least one fungicide as solo-formulation or combined-formulations by the ultra-low volume method, or to inject the composition according to the present invention as a composition or as sole-formulations into the soil (in-furrow).

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

The amount of the biological control agent which is used or employed in combination with an insecticide (I), optionally in the presence of at least one additional insecticide (II) and/or at least one fungicide, depends on the final formulation as well as size or type of the plant, plant parts, seeds, harvested fruits and vegetables to be treated.

Usually, the biological control agent to be employed or used according to the invention is present in about 2% to about 80% (w/w), preferably in about 5% to about 75% (w/w), more preferably about 10% to about 70% (w/w) of its solo-formulation or combined-formulation with the at least one insecticide (I), and optionally the at least one additional insecticide (II) and/or at least one fungicide.

In a preferred embodiment *Paecilomyces lilacinus* strain 251 e.g. its spores are present in a solo-formulation or the combined-formulation in a concentration of at least $10^4$ colony forming units per gram preparation (e. g. cells/g preparation, spores/g preparation), such as $10^4$-$10^{11}$ cfu/g, preferably $10^5$-$10^{10}$ cfu/g, more preferably $10^7$-$10^8$ cfu/g, such as $10^8$ cfu/g, $10^9$ cfu/g, $5 \times 10^9$ cfu/g, $10^{10}$ cfu/g or $5 \times 10^{10}$ cfu/g, *Trichoderma atroviride* SC1 e.g. its spores are present in a solo-formulation or the combined-formulation in a concentration of at least $10^1$ colony forming units per gram preparation (e. g. cells/g preparation, spores/g preparation), such as $10^1$-$10^5$ cfu/g, preferably $10^2$-$10^3$ cfu/g, and *Coniothyrium minitans* CON/M/91-08 e.g. its spores are present in a solo-formulation or the combined-formulation in a concentration of at least $10^5$ colony forming units per gram preparation (e. g. cells/g preparation, spores/g preparation), such as $10^5$-$10^{17}$ cfu/g, preferably $10^7$-$10^{15}$ cfu/g, more preferably $10^{10}$-$10^{13}$ cfu/g at the time point of applying biological control agents on a plant or plant parts such as seeds, fruits or vegetables. Also references to the concentration of biological control agents in form of, e.g., spores or cells—when discussing ratios between the amount of a preparation of at least one biological control agent and the amount of the insecticide—are made in view of the time point when the biological control agent is applied on a plant or plant parts such as seeds, fruits or vegetables.

Also the amount of the at least one insecticide (I) which is used or employed in combination with the biological control agent, optionally in the presence of at least one additional insecticide (II) and/or at least one fungicide, depends on the final formulation as well as size or type of the plant, plant parts, seeds, harvested fruit or vegetable to be treated. Usually, the insecticide (I) to be employed or used according to the invention is present in about 0.1% to about 80% (w/w), preferably 1% to about 60% (w/w), more preferably about 10% to about 50% (w/w) of its solo-formulation or combined-formulation with the biological control agent, and optionally at least one additional insecticide (II) and/or at least one fungicide.

The at least one biological control agent and at least one insecticide (I), and if present also the at least one additional insecticide (II) and/or at least one fungicide are used or employed in a synergistic weight ratio. The skilled person is able to find out the synergistic weight ratios for the present invention by routine methods. The skilled person understands that these ratios refer to the ratio within a combined-formulation as well as to the calculative ratio of the at least one biological control agent described herein and the insecticide (I) when both components are applied as mono-formulations to a plant to be treated. The skilled person can calculate this ratio by simple mathematics since the volume and the amount of the biological control agent and insecticide, respectively, in a mono-formulation is known to the skilled person.

The ratio can be calculated based on the amount of the at least one insecticide (I), at the time point of applying said component of a combination according to the invention to a plant or plant part and the amount of a biological control agent shortly prior (e.g., 48 h, 24 h, 12 h, 6 h, 2 h, 1 h) or at the time point of applying said component of a combination according to the invention to a plant or plant part.

The application of the at least one biological control agent and the at least one insecticide (I) to a plant or a plant part can take place simultaneously or at different times as long as both components are present on or in the plant after the application(s). In cases where the biological control agent and the insecticide (I) are applied at different times and the insecticide (I) is applied noticeable prior to the biological control agent, the skilled person can determine the concentration of the insecticide (I) on/in a plant by chemical analysis known in the art, at the time point or shortly before the time point of applying the biological control agent. Vice versa, when the biological control agent is applied to a plant first, the concentration of a biological control agent can be determined using test which are also known in the art, at the time point or shortly before the time point of applying the insecticide (I).

In particular, in one embodiment the synergistic weight ratio of the at least one biological control agent/spore preparation and the at least one insecticide (I) lies in the range of 1:500 to 1000:1, preferably in the range of 1:500 to 500:1, more preferably in the range of 1:500 to 300:1. It has to be noted that these ratio ranges refer to the biological control agent/spores preparation (to be combined with at least one insecticide (I) or a preparation of at least one insecticide (I)) of around $10^{10}$ cells/spores per gram preparation of said cells/spores. For example, a ratio of 100:1 means 100 weight parts of a biological control agent/spore preparation having a cell/spore concentration of $10^{10}$ cells/spores per gram preparation and 1 weight part of the insecticide are combined (either as a solo formulation, a combined formulation or by separate applications to plants so that the combination is formed on the plant).

In another embodiment, the synergistic weight ratio of the at least one biological control agent/spore preparation to the insecticide (I) is in the range of 1:100 to 65000:1, such as 62500:1 or 31250:1, preferably in the range of 1:100 to 20.000:1, preferably in the range of 1:50 to 10.000:1, such as 100:1, 250:1, 500:1, 533:1, 1066:1 (1066,67:1), 2.500:1, 1:6250, 8000:1, 1:10000 or 12.500:1, or even in the range of 1:50 to 1000:1, such as 100:1, 250:1 or 500:1, 1000:1. Once again the mentioned ratios ranges refer to biological control agent/spore preparations of biological control agents of around $10^{10}$ cells or spores per gram preparation of said biological control agent or where defined elsewhere (see e. g. examples).

The cell/spore concentration of preparations can be determined by applying methods known in the art. To compare weight ratios of the biological control agent/spore preparation to the insecticide (I), the skilled person can easily determine the factor between a preparation having a biological control agent/spore concentration different from $10^{10}$ cells/spores per gram cell/spore preparation and a preparation having a biological control agent/spore concentration of $10^{10}$ cells/spores per gram preparation to calculate whether a ratio of a biological control agent/spore preparation to the insecticide is within the scope of the above listed ratio ranges.

In one embodiment of the present invention, the concentration of the biological control agent after dispersal is at least 50 g/ha, such as 50-7500 g/ha, 50-2500 g/ha, 50-1500 g/ha; at least 250 g/ha (hectare), at least 500 g/ha or at least 800 g/ha.

The application rate of composition to be employed or used according to the present invention may vary. The skilled person is able to find the appropriate application rate by way of routine experiments.

Seed Treatment

In another aspect of the present invention a seed treated with the composition as described above is provided.

The control of insects, nematodes and/or phytopathogens by treating the seed of plants has been known for a long time and is a subject of continual improvements.

Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by insects, nematodes and/or phytopathogens, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present invention therefore also relates in particular to a method for protecting seed and germinating plants from attack by pests, by treating the seed with at least one biological control agent as defined above and/or a mutant of it having all identifying characteristics of the respective strain, and/or at least one metabolite produced by the respective strain that exhibits activity against insects, nematodes and/or phytopathogens and at least one insecticide (I) and optionally at least one additional insecticide (II) and/or at least one fungicide of the invention. The method of the invention for protecting seed and germinating plants from attack by pests encompasses a method in which the seed is treated simultaneously in one operation with the at least one biological control agent and the at least one insecticide (I), and optionally the at least one additional insecticide (II) and/or at least one fungicide. It also encompasses a method in which the seed is treated at different times with the at least one biological control agent and the at least one insecticide (I), and optionally the at least one additional insecticide (II) and/or at least one fungicide.

The invention relates to the use of the composition of the invention for treating seed for the purpose of protecting the seed and the resultant plant against insects, mites, nematodes and/or phytopathogens.

The invention also relates to seed which at the same time has been treated with at least one biological control agent and at least one insecticide (I), and optionally at least one additional insecticide (II) and/or at least one fungicide. The invention further relates to seed which has been treated at different times with the at least one biological control agent and the at least one insecticide (I), and optionally at least one additional insecticide (II) and/or at least one fungicide. In the case of seed which has been treated at different times with the at least one biological control agent and the at least one insecticide (I), and optionally the at least one additional insecticide (II) and/or at least one fungicide, the individual active ingredients in the composition of the invention may be present in different layers on the seed.

Furthermore, the invention relates to seed which, following treatment with the composition of the invention, is subjected to a film-coating process in order to prevent dust abrasion of the seed.

One of the advantages of the present invention is that, owing to the particular systemic properties of the compositions of the invention, the treatment of the seed with these compositions provides protection from insects, nematodes and/or phytopathogens not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with composition of the invention, germination and emergence of the treated seed may be promoted.

It is likewise considered to be advantageous composition of the invention may also be used, in particular, on transgenic seed.

It is also stated that the composition of the invention may be used in combination with agents of the signalling technology, as a result of which, for example, colonization with symbionts is improved, such as rhizobia, mycorrhiza and/or endophytic bacteria, for example, is enhanced, and/or nitrogen fixation is optimized.

The compositions of the invention are suitable for protecting seed of any variety of plant which is used in agriculture, in greenhouses, in forestry or in horticulture. More particularly, the seed in question is that of cereals (e.g. wheat, barley, rye, oats and millet), maize, cotton, soybeans, rice, potatoes, sunflower, coffee, tobacco, canola, oilseed rape, beets (e.g. sugar beet and fodder beet), peanuts, vegetables (e.g. tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

As already mentioned above, the treatment of transgenic seed with the composition of the invention is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the composition of the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The combinations which can be used in accordance with the invention may be converted into the customary seed-dressing formulations, such as solutions, emulsions, suspensions, powders, foams, slurries or other coating compositions for seed, and also ULV formulations.

These formulations are prepared in a known manner, by mixing composition with customary adjuvants, such as, for example, customary extenders and also solvents or diluents, colorants, wetters, dispersants, emulsifiers, antifoams, preservatives, secondary thickeners, stickers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetters which may be present in the seed-dressing formulations which can be used in accordance with the invention include all of the substances which promote wetting and which are customary in the formulation of active agrochemical ingredients. Use may be made preferably of alkylnaphthalenesulphonates, such as diisopropyl- or diisobutyl-naphthalenesulphonates.

Dispersants and/or emulsifiers which may be present in the seed-dressing formulations which can be used in accordance with the invention include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these. Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magnesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz-und Schädlingsbekämpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the at least one biological control agent and the at least one insecticide (I) in the formulations, and by the seed. The application rates in the case of the composition are situated generally at between 0.001 and 50 g per kilogram of seed, preferably between 0.01 and 15 g per kilogram of seed.

The composition according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in protection of stored products and of materials, and in the hygiene sector. They can be preferably employed as plant protection agents. In particular, the present invention relates to the use of the composition according to the invention as pesticide.

The present composition preferably is active against normally sensitive and resistant species and against all or some stages of development. The abovementioned pests include: pests from the phylum Arthropoda, especially from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici*;

from the class Chilopoda, for example, *Geophilus* spp., *Scutigera* spp.;

from the order or the class Collembola, for example, *Onychiurus armatus*;

from the class Diplopoda, for example, *Blaniulus guttulatus*;

from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*;

from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricorne*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizo-*

*bius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;

from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;

from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order Homoptera, for example, *Acizzia acaciae-baileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma piri*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisni-* gri, *Nephotettix* spp., *Nettigoniclla spectra, Nilaparvata lugens, Oncometopia* spp., *Orthezia praelonga, Oxya chinensis, Pachypsylla* spp., *Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Prosopidopsylla flava, Protopulvinaria pyriformis, Pseudaulacaspis pentagona, Pseudococcus* spp., *Psyllopsis* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoideus titanus, Schizaphis graminum, Selenaspidus articulatus, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii, Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis, Sirex* spp., *Solenopsis invicta, Tapinoma* spp., *Urocerus* spp., *Vespa* spp., *Xeris* spp.;

from the order Isopoda, for example, *Armadillidium vulgare, Oniscus asellus, Porcellio scaber;* from the order Isoptera, for example, *Coptotermes* spp., *Cornitermes cumulans, Cryptotermes* spp., *Incisitermes* spp., *Microtermes obesi, Odontotermes* spp., *Reticulitermes* spp.;

from the order Lepidoptera, for example, *Achroia grisella, Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamstra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudaletia unipuncta, Pseudoplusia includens, Pyrausta nubilalis, Rachiplusia nu, Schoenobius* spp., *Scirpophaga* spp., *Scirpophaga innotata, Scotia segetum, Sesamia* spp., *Sesamia inferens, Sparganothis* spp., *Spodoptera* spp., *Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., *Tryporyza incertulas, Tuta absoluta, Virachola* spp.;

from the order Orthoptera or Saltatoria, for example, *Acheta domesticus, Dichroplus* spp., *Gryllotalpa* spp., *Hieroglyphus* spp., *Locusta* spp., *Melanoplus* spp., *Schistocerca gregaria;* from the order Phthiraptera, for example, *Damalinia* spp., *Haematopinus* spp., *Linognathus* spp., *Pediculus* spp., *Ptirus pubis, Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans, Tunga penetrans, Xenopsylla cheopsis;* from the order Thysanoptera, for example, *Anaphothrips obscurus, Baliothrips biformis, Drepanothrips reuteri, Enneothrips flavens, Frankliniella* spp., *Heliothrips* spp., *Hercinothrips femoralis, Rhipiphorothrips cruentatus, Scirtothrips* spp., *Taeniothrips cardamomi, Thrips* spp.;

from the order Zygentoma (=Thysanura), for example, *Ctenolepisma* spp., *Lepisma saccharina, Lepismodes inquilinus, Thermobia domestica;* from the class Symphyla, for example, *Scutigerella* spp.;

pests from the phylum Mollusca, especially from the class Bivalvia, for example, *Dreissena* spp., and from the class Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests from the phylums Plathelminthes and Nematoda, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* phytoparasitic pests from the phylum Nematoda, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp., *Hirschmaniella* spp, *Tetylenchus* spp.

It is furthermore possible to control organisms from the subphylum Protozoa, especially from the order Coccidia, such as *Eimeria* spp.

Furthermore, the composition according to the present invention has potent microbiciodal activity and can be used for control of unwanted microorganisms, such as fungi and bacteria, in crop protection and in the protection of materials.

The invention also relates to a method for controlling unwanted microorganisms, characterized in that the inventive composition is applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia* recondite, *P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;
wilt diseases caused, for example, by *Monilinia* species, for example *Monilinia laxa*;
leaf blister or leaf curl diseases caused, for example, by *Exobasidium* species, for example *Exobasidium vexans*; *Taphrina* species, for example *Taphrina deformans*;
decline diseases of wooden plants caused, for example, by Esca disease, caused for example by *Phaemoniella clamydospora, Phaeoacremonium aleophilum* and *Fomitiporia mediterranea*; Eutypa dyeback, caused for example by *Eutypa lata*;
*Ganoderma* diseases caused for example by *Ganoderma boninense*; *Rigidoporus* diseases caused for example by *Rigidoporus lignosus*;
diseases of flowers and seeds caused, for example, by *Botrytis* species, for example *Botrytis cinerea*;
diseases of plant tubers caused, for example, by *Rhizoctonia* species, for example *Rhizoctonia solani*; *Helminthosporium* species, for example *Helminthosporium solani*;
Club root caused, for example, by *Plasmodiophora* species, for example *Plamodiophora brassicae*;
diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. truncatum), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive compositions can be used for curative or protective/preventive control of phytopathogenic fungi. The invention therefore also relates to curative and protective methods for controlling phytopathogenic fungi by the use of the inventive composition, which is applied to the seed, the plant or plant parts, the fruit or the soil in which the plants grow.

The fact that the composition is well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive composition, when it is well tolerated by plants, has favourable homeotherm toxicity and is well tolerated by the environment, is suitable for protecting plants and plant organs, for enhancing harvest yields, for improving the quality of the harvested material. It can preferably be used as crop protection composition. It is active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata*, Arecaceae sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. Rosaceae sp. (e.g. pome fruits such as apples and pears, but also stone fruits such as apricots, cherries, almonds, plums and peaches, and berry fruits such as strawberries, raspberries, red and black currant and gooseberry), Ribesioidae sp., Juglandaceae sp., Betulaceae sp., Anacardiaceae sp., Fagaceae sp., Moraceae sp., Oleaceae sp. (e.g. olive tree), Actinidaceae sp., Lauraceae sp. (e.g. avocado, cinnamon, camphor), Musaceae sp. (e.g. banana trees and plantations), Rubiaceae sp. (e.g. coffee), Theaceae sp. (e.g. tea), Sterculiceae sp., Rutaceae sp. (e.g. lemons, oranges, mandarins and grapefruit); Solanaceae sp. (e.g. tomatoes, potatoes, peppers, capsicum, aubergines, tobacco), Liliaceae sp., Compositae sp. (e.g. lettuce, artichokes and chicory—including root chicory, endive or common chicory), Umbelliferae sp. (e.g. carrots, parsley, celery and celeriac), Cucurbitaceae sp. (e.g. cucumbers—including gherkins, pumpkins, watermelons, calabashes and melons), Alliaceae sp. (e.g. leeks and onions), Cruciferae sp. (e.g. white cabbage, red cabbage, broccoli, cauliflower, Brussels sprouts, pak choi, kohlrabi, radishes, horseradish, cress and chinese cabbage), Leguminosae sp. (e.g. peanuts, peas, lentils and beans—e.g. common beans and broad beans), Chenopodiaceae sp. (e.g. Swiss chard, fodder beet, spinach, beetroot), Linaceae sp. (e.g. hemp), Cannabeacea sp. (e.g. cannabis), Malvaceae sp. (e.g. okra, cocoa), Papaveraceae (e.g. poppy), Asparagaceae (e.g. asparagus); useful plants and ornamental plants in the garden and woods including turf, lawn, grass and *Stevia rebaudiana*; and in each case genetically modified types of these plants.

Depending on the plant species or plant cultivars, their location and growth conditions (soils, climate, vegetation period, diet), using or employing the composition according to the present invention the treatment according to the invention may also result in super-additive ("synergistic") effects. Thus, for example, by using or employing inventive composition in the treatment according to the invention, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the inventive composition in the treatment according to the invention may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses, Thus, by using or employing composition according to the present invention in the treatment according to the invention, plants can be protected against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses, i. e. that already exhibit an increased plant health with respect to stress tolerance. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance. Preferably, the treatment of these plants and cultivars with the composition of the present invention additionally increases the overall plant health (cf. above).

Plants and plant cultivars which may also be treated according to the invention, are those plants characterized by enhanced yield characteristics i. e. that already exhibit an increased plant health with respect to this feature. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability. Preferably, the treatment of these plants and cultivars with the composition of the present invention additionally increases the overall plant health (cf. above).

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an Eleusine EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) An insecticidal crystal protein from *Bacillus thuringiensis* or an insecticidal portion thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, e.g. proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose) polymerase (PARP) gene in the plant cells or plants b. plants which contain a stress tolerance enhancing transgene capable of reducing the expression and/or the activity of the poly(ADP-ribose)glycohydrolase (PARG) encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1, 4-glucans, plants producing alternan, 3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes, b) Plants, such as cotton plants, containing an altered form of rsw2 or rsw3 homologous nucleic acids, c) Plants, such as cotton plants, with increased expression of sucrose phosphate synthase, d) Plants, such as cotton plants, with increased expression of sucrose synthase, e) Plants, such as cotton plants, wherein the timing of the plasmodesmatal gating at the basis of the fiber cell is altered, e.g. through downregulation of fiberselective β 1,3-glucanase, f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content, b) Plants such as oilseed rape plants, producing oil having a low linolenic acid content, c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 06/128569); Event 1143-51B (cotton, insect control, not deposited, described in WO 06/128570); Event 1445 (cotton, herbicide tolerance, not deposited, described in US-A 2002-120964 or WO 02/034946); Event 17053 (rice, herbicide tolerance, deposited as PTA-9843, described in WO 10/117737); Event 17314 (rice, herbicide tolerance, deposited as PTA-9844, described in WO 10/117735); Event 281-24-236 (cotton, insect control—herbicide tolerance, deposited as PTA-6233, described in WO 05/103266 or US-A 2005-216969); Event 3006-210-23 (cotton, insect control—herbicide tolerance, deposited as PTA-6233, described in US-A 2007-143876 or WO 05/103266); Event 3272 (corn, quality trait, deposited as PTA-9972, described in WO 06/098952 or US-A 2006-230473); Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO 11/075595); Event 5307 (corn, insect control, deposited as ATCC PTA-9561, described in WO 10/077816); Event ASR-368 (bent grass, herbicide tolerance, deposited as ATCC PTA-4816, described in US-A 2006-162007 or WO 04/053062); Event B16 (corn, herbicide tolerance, not deposited, described in US-A 2003-126634); Event BPS-CV127-9 (soybean, herbicide tolerance, deposited as NCIMB No. 41603, described in WO 10/080829); Event CE43-67B (cotton, insect control, deposited as DSM ACC2724, described in US-A 2009-217423 or WO 06/128573); Event CE44-69D (cotton, insect control, not deposited, described in US-A 2010-0024077); Event CE44-69D (cotton, insect control, not deposited, described in WO 06/128571); Event CE46-02A (cotton, insect control, not deposited, described in WO 06/128572); Event COT102 (cotton, insect control, not deposited, described in US-A 2006-130175 or WO 04/039986); Event COT202 (cotton, insect control, not deposited, described in US-A 2007-067868 or WO 05/054479); Event COT203 (cotton, insect control, not deposited, described in WO 05/054480); Event DAS40278 (corn, herbicide tolerance, deposited as ATCC PTA-10244, described in WO 11/022469); Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO 09/100188); Event DAS68416 (soybean, herbicide tolerance, deposited as ATCC PTA-10442, described in WO 11/066384 or WO 11/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO 08/054747); Event DP-32138-1 (corn, hybridization system, deposited as ATCC PTA-9158, described in US-A 2009-0210970 or WO 09/103049); Event DP-356043-5 (soybean, herbicide tolerance, deposited as ATCC PTA-8287, described in US-A 2010-0184079 or WO 08/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO 08/151780); Event GHB614 (cotton, herbicide tolerance, deposited as ATCC PTA-6878, described in US-A 2010-050282 or WO 07/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 10/076212); Event H7-1 (sugar beet, herbicide tolerance, deposited as NCIMB 41158 or NCIMB 41159, described in US-A 2004-172669 or WO 04/074492); Event JOPLIN1 (wheat, disease tolerance, not deposited, described in US-A 2008-064032); Event LL27 (soybean, herbicide tolerance, deposited as NCIMB41658, described in WO 06/108674 or US-A 2008-320616); Event LL55 (soybean, herbicide tolerance, deposited as NCIMB 41660, described in WO 06/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 05/061720); Event MIR162 (corn, insect control, deposited as PTA-8166, described in US-A 2009-300784 or WO 07/142840); Event MIR604 (corn, insect control, not deposited, described in US-A 2008-167456 or WO 05/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 04/011601 or US-A 2006-095986); Event MON87427 (corn, pollination control, deposited as ATCC PTA-7899, described in WO 11/062904); Event MON87460 (corn, stress tolerance, deposited as ATCC PTA-8910, described in WO 09/111263 or US-A 2011-0138504); Event MON87701 (soybean, insect control, deposited as ATCC PTA-8194, described in US-A 2009-130071 or WO 09/064652); Event MON87705 (soybean, quality trait—herbicide tolerance, deposited as ATCC PTA-9241, described in US-A 2010-0080887 or WO 10/037016); Event MON87708 (soybean, herbicide tolerance, deposited as ATCC PTA9670, described in WO 11/034704); Event MON87754 (soybean, quality trait, deposited as ATCC PTA-9385, described in WO 10/024976); Event MON87769 (soybean, quality trait, deposited as ATCC PTA-8911, described in US-A 2011-0067141 or WO 09/102873); Event MON88017 (corn, insect control—herbicide tolerance, deposited as ATCC PTA-5582, described in US-A 2008-028482 or WO 05/059103); Event MON88913 (cotton, herbicide tolerance, deposited as ATCC PTA-4854, described in WO 04/072235 or US-A 2006-059590); Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO 06/130436); Event MS11 (oilseed rape, pollination control—herbicide tolerance, deposited as ATCC PTA-850 or PTA-2485, described in WO 01/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 08/114282); Event RF3 (oilseed rape, pollination control—herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control—herbicide tolerance, deposited as ATCC PTA-8171, described in US-A 2010-077501 or WO 08/122406); Event T342-142 (cotton, insect control, not deposited, described in WO 06/128568); Event TC1507 (corn, insect control—herbicide tolerance, not deposited, described in US-A 2005-039226 or WO 04/099447); Event VIP1034 (corn, insect control—herbicide tolerance, deposited as ATCC PTA-3925., described in WO 03/052073), Event 32316 (corn, insect control-herbicide tolerance, deposited as PTA-11507, described in WO 11/084632), Event 4114 (corn, insect control-herbicide tolerance, deposited as PTA-11506, described in WO 11/084621).

Particularly useful transgenic plants which may be treated according to the invention are plants containing transformation events, or combination of transformation events, that are listed for example in the databases from various national or regional regulatory agencies.

In a final aspect the present invention relates to a method of controlling nematodes or insects in the soil surrounding a plant comprising applying an effective amount of the composition according to the invention to said soil.

The examples illustrate the invention.

Formula for the efficacy of the combination of two compounds

The expected efficacy of a given combination of two compounds is calculated as follows (see Colby, S.R., "Calculating Synergistic and antagonistic Responses of Herbicide Combinations", Weeds 15, pp. 20-22, 1967):

If
X is the efficacy expressed in % mortality of the untreated control for test compound A at a concentration of m ppm respectively m g/ha,
Y is the efficacy expressed in % mortality of the untreated control for test compound B at a concentration of n ppm respectively n g/ha,
E is the efficacy expressed in % mortality of the untreated control using the mixture of A and B at m and n ppm respectively m and n g/ha,
then is $$E = X + Y - \frac{X \times Y}{100}$$

If the observed insecticidal efficacy of the combination is higher than the one calculated as "E", then the combination of the two compounds is more than additive, i.e., there is a synergistic effect.

EXAMPLE A

*Phaedon cochleariae*—Spray Test

Solvent: 78.0 parts by weight of acetone
1.5 parts by weight of dimethylformamide
Emulsifier: alkylaryl polyglycol ether To produce a suitable preparation of active compound, 1 part by weight of active compound is mixed with the stated amount of solvents and is diluted with water, containing an emulsifier concentration of 1000 ppm, to the desired concentration. To produce a suitable preparation of a spore suspension the spores are diluted with emulsifier containing water to the desired concentration. Further test concentrations are prepared by dilution with emulsifier containing water.

Chinese cabbage (*Brassica pekinensis*) leaf-disks are sprayed with a preparation of the active ingredient of the desired concentration. Once dry, the leaf disks are infested with mustard beetle larvae (*Phaedon cochleariae*).

After the specified period of time, mortality in % is determined. 100% means all beetle larvae have been killed and 0% means none of the beetle larvae have been killed. The mortality values determined thus are recalculated using the Colby-formula (see sheet 1).

According to the present application in this test e.g. the following combinations show a synergistic effect in comparison to the single compounds:

TABLE A-1

*Phaedon cochleariae* - test

| Active Ingredient | Concentration/Application rate in g ai/ha | Efficacy in % after $2^d$ |
|---|---|---|
| BioAct WG *Paecilomyces lilacinus* strain 251 (BioAct, 1 × 10¹⁰ spores/g) | 2500 2000 | 0 0 |
| Contans WG *Coniothyrium minitans* (1 × 10⁹ spores/g) | 2000 | 0 |
| Cyantraniliprole | 4 | 0 |

TABLE A-1-continued

*Phaedon cochleariae* - test

| Active Ingredient | Concentration/Application rate in g ai/ha | Efficacy in % after $2^d$ | |
|---|---|---|---|
| | | obs.* | cal.** |
| BioAct WG + Cyantraniliprole (500:1) according to the invention | 2000 + 4 | 100 | 0 |
| | | obs.* | cal.** |
| Contans WG + Cyantraniliprole (500:1) according to the invention | 2000 + 4 | 100 | 0 |

TABLE A-2

*Phaedon cochleariae* - test

| Active Ingredient | Concentration/Application rate in g ai/ha | Efficacy in % after $6^d$ | |
|---|---|---|---|
| BioAct WG *Paecilomyces lilacinus* strain 251 (BioAct, 1 × 1010 spores/g) | 2500 2000 | 0 0 | |
| Contans WG *Coniothyrium minitans* (1 × 10⁹ spores/g) | 2000 | 0 | |
| Chlorantraniliprole | 0.8 | 33 | |
| | | obs.* | cal.** |
| BioAct WG + Chlorantraniliprole (2500:1) according to the invention | 2000 + 0.8 | 67 | 33 |
| Cyantraniliprole | 0.8 | 0 | |
| | | obs.* | cal.** |
| BioAct WG + Cyantraniliprole (2500:1) according to the invention | 2000 + 0.8 | 100 | 0 |
| | | obs.* | cal.** |
| Contans WG + Cyantraniliprole (2500:1) according to the invention | 2000 + 0.8 | 83 | 0 |
| Methiocarb | 10 | 50 | |
| | | obs.* | cal.** |
| BioAct WG + Methiocarb (250:1) according to the invention | 2500 + 10 | 83 | 50 |

*obs. = observed insecticidal efficacy,
**cal. = efficacy calculated with Colby-formula

Example B

Spodoptera frugiperda—Spray Test

Solvent: 78.0 parts by weight acetone
1.5 parts by weight dimethylformamide
Emulsifier: alkylaryl polyglycol ether To produce a suitable preparation of active compound, 1 part by weight of active compound is mixed with the stated amount of solvents and is diluted with water, containing an emulsifier concentration of 1000 ppm, to the desired concentration. To produce a suitable preparation of a spore suspension the spores are diluted with emulsifier containing water to the desired concentration. Further test concentrations are prepared by dilution with emulsifier containing water.

Maize (*Zea mais*) leaf sections are sprayed with a preparation of the active ingredient of the desired concentration. Once dry, the leaf sections are infested with fall armyworm larvae (*Spodoptera frugiperda*).

After the specified period of time, mortality in % is determined. 100% means all caterpillars have been killed and 0% means none of the caterpillars have been killed. The mortality values determined thus are recalculated using the Colby-formula (see sheet 1).

According to the present application in this test e.g. the following combinations show a synergistic effect in comparison to the single compounds:

TABLE B-1

*Spodoptera frugiperda* - test

| Active Ingredient | Concentration/Application rate in g ai/ha | Efficacy in % after $2^d$ | |
|---|---|---|---|
| BioAct WG *Paecilomyces lilacinus* strain 251 (BioAct, 1 × 10$^{10}$ spores/g) | 4000 | 0 | |
| Contans WG *Coniothyrium minitans* (1 × 10$^9$ spores/g) | 4000 | 0 | |
| | 2500 | 0 | |
| Chlorantraniliprole | 0.8 | 67 | |
| | | obs.* | cal.** |
| BioAct WG + Chlorantraniliprole (2500:1) according to the invention | 2000 + 0.8 | 100 | 67 |
| | | obs.* | cal.** |
| Contans WG + Chlorantraniliprole (2500:1) according to the invention | 2000 + 0.8 | 100 | 67 |
| Spinetoram | 0.08 | 67 | |
| | | obs.* | cal.** |
| Contans WG + Spinetoram (31250:1) according to the invention | 2500 + 0.08 | 100 | 67 |
| Spinosad | 4 | 50 | |
| | | obs.* | cal.** |
| BioAct WG + Spinosad (500:1) according to the invention | 2000 + 4 | 83 | 50 |
| Thiodicarb | 7.5 | 67 | |
| | 3.75 | 0 | |

TABLE B-1-continued

*Spodoptera frugiperda* - test

| Active Ingredient | Concentration/Application rate in g ai/ha | Efficacy in % after $2^d$ | |
|---|---|---|---|
| | | obs.* | cal.** |
| BioAct WG + Thiodicarb (1066.67:1) according to the invention | 4000 + 3.75 | 50 | 0 |
| Contans WG + Thiodicarb | | obs.* | cal.** |
| (533.33:1) | 4000 + 7.5 | 100 | 67 |
| (1066.67:1) according to the invention | 4000 + 3.75 | 50 | 0 |

TABLE B-2

*Spodoptera frugiperda* - test

| Active Ingredient | Concentration/Application rate in g ai/ha | Efficacy in % after $6^d$ | |
|---|---|---|---|
| BioAct WG *Paecilomyces lilacinus* strain 251 (BioAct, 1 × 10$^{10}$ spores/g) | 4000 | 0 | |
| | 2000 | 0 | |
| Contans WG *Coniothyrium minitans* (1 × 10$^9$ spores/g) | 4000 | 0 | |
| | 2000 | 0 | |
| Clothianidin | 20 | 0 | |
| | | obs.* | cal.** |
| BioAct WG + Clothianidin (100:1) according to the invention | 2000 + 20 | 100 | 0 |
| Chlorantraniliprole | 0.16 | 0 | |
| | | obs.* | cal.** |
| BioAct WG + Chlorantraniliprole (12500:1) according to the invention | 2000 + 0.16 | 33 | 0 |
| | | obs.* | cal.** |
| Contans WG + Chlorantraniliprole (12500:1) according to the invention | 2000 + 0.16 | 67 | 0 |
| Spinetoram | 0.032 | 0 | |
| | | obs.* | cal.** |
| BioAct WG + Spinetoram (62500:1) according to the invention | 2000 + 0.032 | 67 | 0 |
| Spinosad | 0.8 | 0 | |
| | | obs.* | cal.** |
| BioAct WG + Spinosad (2500:1) according to the invention | 2000 + 0.8 | 33 | 0 |
| Thiodicarb | 3.75 | 0 | |

TABLE B-2-continued

Spodoptera frugiperda - test

| Active Ingredient | Concentration/ Application rate in g ai/ha | Efficacy in % after $6^d$ | |
|---|---|---|---|
| | | obs.* | cal.** |
| BioAct WG + Thiodicarb (1066.67:1) according to the invention | 4000 + 3.75 | 67 | 0 |
| | | obs.* | cal.** |
| Contans WG + Thiodicarb (1066.67:1) according to the invention | 4000 + 3.75 | 67 | 0 |

*obs. = observed insecticidal efficacy,
**cal. = efficacy calculated with Colby-formula Example C Myzus persicae—Spray Test Solvent: 78.0 parts by weight acetone
1.5 parts by weight dimethylformamide
Emulsifier: alkylaryl polyglycol ether To produce a suitable preparation of active compound, 1 part by weight of active compound is mixed with the stated amount of solvents and is diluted with water, containing an emulsifier concentration of 1000 ppm, to the desired concentration. To produce a suitable preparation of a spore suspension the spores are diluted with emulsifier containing water to the desired concentration. Further test concentrations are prepared by dilution with emulsifier containing water.

Chinese cabbage (Brassica pekinensis) leaf-disks infected with all instars of the green peach aphid (Myzus persicae) are sprayed with a preparation of the active ingredient of the desired concentration.

After the specified period of time, mortality in % is determined. 100% means all aphids have been killed; 0% means none of the aphids have been killed. The mortality values determined thus are recalculated using the Colby-formula (see sheet 1).

According to the present application in this test e.g. the following combinations show a synergistic effect in comparison to the single compounds:

TABLE C

Myzus persicae - test

| Active Ingredient | Concentration/ Application rate in g ai/ha | Efficacy in % after $1^d$ | |
|---|---|---|---|
| BioAct WG aecilomyces lilacinus strain 251 (BioAct, 1 × 1010 spores/g) | 2000 | 0 | |
| Thiacloprid | 4 | 0 | |
| | | obs.* | cal.** |
| BioAct WG + Thiacloprid (500:1) according to the invention | 2000 + 4 | 90 | 0 |
| Thiamethoxam | 0.8 | 0 | |

TABLE C-continued

Myzus persicae - test

| Active Ingredient | Concentration/ Application rate in g ai/ha | Efficacy in % after $1^d$ | |
|---|---|---|---|
| | | obs.* | cal.** |
| BioAct WG + Thiamethoxam (2500:1) according to the invention | 2000 + 0.8 | 70 | 0 |

Example D

Tetranychus urticae—Spray Test, OP-Resistant

Solvent: 78.0 parts by weight acetone
1.5 parts by weight dimethylformamide
Emulsifier: alkylaryl polyglycol ether To produce a suitable preparation of active compound, 1 part by weight of active compound is mixed with the stated amount of solvents and is diluted with water, containing an emulsifier concentration of 1000 ppm, to the desired concentration. To produce a suitable preparation of a spore suspension the spores are diluted with emulsifier containing water to the desired concentration. Further test concentrations are prepared by dilution with emulsifier containing water.

French beans (Phaseolus vulgaris) which are heavily infested with all stages of the two spotted spidermite (Tetranychus urticae), are sprayed with a preparation of the active ingredient of the desired concentration.

After the specified period of time, mortality in % is determined. 100% means all spider mites have been killed and 0% means none of the spider mites have been killed. The mortality values determined thus are recalculated using the Colby-formula (see sheet 1).

According to the present application in this test e.g. the following combinations show a synergistic effect in comparison to the single compounds:

TABLE D-1

Tetranychus urticae - test

| Active Ingredient | Concentration/ Application rate in g ai/ha | Efficacy in % after $2^d$ | |
|---|---|---|---|
| Contans WG Coniothyrium minitans (1 × $10^9$ spores/g) | 2500 2000 | 0 0 | |
| Spinetoram | 0.4 | 0 | |
| | | obs.* | cal.** |
| Contans WG + Spinetoram (6.250:1) according to the invention | 2500 + 0.4 | 70 | 0 |
| Thiacloprid | 20 | 40 | |
| | | obs.* | cal.** |
| Contans WG + Thiacloprid (100:1) according to the invention | 2000 + 20 | 80 | 40 |

*obs. = observed insecticidal efficacy,
**cal. = efficacy calculated with Colby-formula

TABLE D-2

Tetranychus urticae - test

| Active Ingredient | Concentration/ Application rate in g ai/ha | Efficacy in % after $6^d$ | |
|---|---|---|---|
| BioAct WG *Paecilomyces lilacinus* strain 251 (BioAct, 1 × 10¹⁰ spores/g) | 2000 | 0 | |
| Contans WG *Coniothyrium minitans* (1 × 10⁹ spores/g) | 2500 | 0 | |
| Spinetoram | 0.08 | 0 | |
| | | obs.* | cal.** |
| Contans WG + Spinetoram (31.250:1) according to the invention | 2500 + 0.08 | 70 | 0 |
| Spinosad | 20 | 0 | |
| | | obs.* | cal.** |
| BioAct WG + Spinosad (100:1) according to the invention | 2000 + 20 | 90 | 0 |

*obs. = observed insecticidal efficacy,
**cal. = efficacy calculated with Colby-formula

The invention claimed is:

1. A composition comprising at least one biological control agent selected from the group consisting of *Paecilomyces lilacinus* strain 251 (AGAL No. 89/030550) and *Coniothyrium minitans* CON/M/91-08 (DSM 9660) and at least one insecticide (I) selected from the group consisting of
   (a) an acetylcholinesterase (AChE) inhibitor which is Thiodicarb,
   (b) a nicotinic acetylcholine receptor (nAChR) agonist selected from the group consisting of Clothianidin and Thiacloprid,
   (c) a nicotinic acetylcholine receptor (nAChR) allosteric activator selected from the group consisting of Spinetoram and Spinosad, and
   (d) a ryanodine receptor modulator selected from the group consisting of Chlorantraniliprole and Cyantraniliprole,
   in a synergistically effective amount.

2. The composition according to claim 1, wherein the insecticide (I) is Clothianidin.

3. The composition according to claim 1, wherein the insecticide (I) is Thiodicarb.

4. The composition according to claim 1, wherein the insecticide (I) is Chlorantraniliprole.

5. The composition according to claim 1 additionally comprising at least one auxiliary selected from the group consisting of extenders, solvents, spontaneity promoters, carriers, emulsifiers, dispersants, frost protectants, thickeners and adjuvants.

6. The composition according to claim 2, wherein the at least one biological control agent is *Paecilomyces lilacinus* strain 251 (AGAL No. 89/030550).

7. A method of controlling insects in the soil surrounding a plant comprising applying an effective amount of the composition according to claim 1 to said soil.

8. A seed treated with a composition comprising at least one biological control agent selected from the group consisting of *Paecilomyces lilacinus* strain 251 (AGAL No. 89/030550) and *Coniothyrium minitans* CON/M/91-08 (DSM 9660)
   and at least one insecticide (I) selected from the group consisting of
   (a) an acetylcholinesterase (AChE) inhibitor which is Thiodicarb,
   (b) a nicotinic acetylcholine receptor (nAChR) agonist selected from the group consisting of Clothianidin and Thiacloprid,
   (c) a nicotinic acetylcholine receptor (nAChR) allosteric activator selected from the group consisting of Spinetoram and Spinosad, and
   (d) a ryanodine receptor modulator selected from the group consisting of Chlorantraniliprole and Cyantraniliprole,
   in a synergistically effective amount.

9. The seed according to claim 8, wherein the insecticide (I) is Clothianidin.

10. The seed according to claim 9, wherein the at least one biological control agent is *Paecilomyces lilacinus* strain 251 (AGAL No. 89/030550).

11. A kit of parts comprising at least one biological control agent selected from the group consisting of *Paecilomyces lilacinus* strain 251 (AGAL No. 89/030550) and *Coniothyrium minitans* CON/M/91-08 (DSM 9660)
    and at least one insecticide (I) selected from the group consisting of
    (a) an acetylcholinesterase (AChE) inhibitor which is Thiodicarb,
    (b) a nicotinic acetylcholine receptor (nAChR) agonist selected from the group consisting of Clothianidin and Thiacloprid,
    (c) a nicotinic acetylcholine receptor (nAChR) allosteric activator selected from the group consisting of Spinetoram and Spinosad, and
    (d) a ryanodine receptor modulator selected from the group consisting of Chlorantraniliprole and Cyantraniliprole,
    in a synergistically effective amount in a spatially separated arrangement.

12. A method for reducing overall damage of plants and plant parts as well as losses in harvested fruits or vegetables caused by insects and/or mites comprising the step of simultaneously or sequentially applying at least one biological control agent selected from the group consisting of *Paecilomyces lilacinus* strain 251 (AGAL No. 89/030550) and *Coniothyrium minitans* CON/M/91-08 (DSM 9660)
    and at least one insecticide (I) selected from the group consisting of
    (a) an acetylcholinesterase (AChE) inhibitor which is Thiodicarb,
    (b) a nicotinic acetylcholine receptor (nAChR) agonist selected from the group consisting of Clothianidin and Thiacloprid,
    (c) a nicotinic acetylcholine receptor (nAChR) allosteric activator selected from the group consisting of Spinetoram and Spinosad, and
    (d) a ryanodine receptor modulator selected from the group consisting of Chlorantraniliprole and Cyantraniliprole,
    on the plant, plant parts, harvested fruits, vegetables and/or plant's locus of growth in a synergistically effective amount.

* * * * *